US008337817B2

(12) United States Patent
Nagata et al.

(10) Patent No.: US 8,337,817 B2
(45) Date of Patent: Dec. 25, 2012

(54) PREPARATION FOR TRANSNASAL APPLICATION

(75) Inventors: Ryoichi Nagata, Kagoshima (JP); Shunji Haruta, Kagoshima (JP)

(73) Assignee: Shin Nippon Biomedical Laboratories, Ltd., Kagoshima (JP)

( * ) Notice: Subject to any disclaimer, the term of this patent is extended or adjusted under 35 U.S.C. 154(b) by 444 days.

(21) Appl. No.: 12/521,116

(22) PCT Filed: Dec. 25, 2007

(86) PCT No.: PCT/JP2007/074787
§ 371 (c)(1),
(2), (4) Date: Mar. 25, 2010

(87) PCT Pub. No.: WO2008/078730
PCT Pub. Date: Jul. 3, 2008

(65) Prior Publication Data
US 2010/0178331 A1    Jul. 15, 2010

(30) Foreign Application Priority Data

Dec. 26, 2006 (JP) ................................. 2006-350094

(51) Int. Cl.
*A61K 9/14* (2006.01)
*A61K 31/19* (2006.01)
*A61K 31/33* (2006.01)
*A61K 31/40* (2006.01)
*A61K 31/44* (2006.01)
*A61K 31/56* (2006.01)
*A61K 31/70* (2006.01)
*A61K 31/727* (2006.01)
*A61K 38/00* (2006.01)
*A61K 38/11* (2006.01)
*A61K 38/18* (2006.01)
*A61K 38/23* (2006.01)
*A61K 38/26* (2006.01)
*A61K 38/27* (2006.01)
*A61K 38/28* (2006.01)
*A61K 38/29* (2006.01)
*A61K 48/00* (2006.01)
*A61K 31/445* (2006.01)
*C12N 15/11* (2006.01)

(52) U.S. Cl. ............ 424/46; 424/489; 514/1.1; 514/5.9; 514/7.2; 514/7.7; 514/10.9; 514/11.3; 514/11.8; 514/11.9; 514/44 A; 514/44 R; 514/50; 514/56; 514/169; 514/183; 514/282; 514/294; 514/304; 514/316; 514/329; 514/420; 514/561; 514/568; 514/888

(58) Field of Classification Search .................... 424/46, 424/489; 514/1.1, 5.9, 7.2, 7.7, 10.9, 11.3, 514/11.8, 11.9, 44 A, 44 R, 50, 56, 169, 183, 514/282, 294, 304, 316, 329, 420, 561, 568, 514/888
See application file for complete search history.

(56) References Cited

U.S. PATENT DOCUMENTS

| 4,013,075 | A | 3/1977 | Cocozza |
| 4,159,345 | A | 6/1979 | Takeo et al. |
| 4,226,233 | A | 10/1980 | Kritzer |
| 4,613,500 | A | 9/1986 | Suzuki et al. |
| 4,889,114 | A | 12/1989 | Kladders |
| 5,647,349 | A | 7/1997 | Ohki et al. |
| 5,683,361 | A | 11/1997 | Elk et al. |
| 5,804,209 | A | 9/1998 | De Ponti et al. |
| 5,810,004 | A | 9/1998 | Ohki et al. |
| 5,942,242 | A | 8/1999 | Mizushima et al. |
| 5,948,749 | A | 9/1999 | Igarashi et al. |
| 5,958,458 | A * | 9/1999 | Norling et al. ................. 424/490 |
| 6,136,295 | A | 10/2000 | Edwards et al. |
| 6,197,328 | B1 | 3/2001 | Yanagawa |
| 6,248,363 | B1 | 6/2001 | Patel et al. |
| 6,273,086 | B1 | 8/2001 | Ohki et al. |
| 6,298,846 | B1 | 10/2001 | Ohki et al. |
| 6,516,795 | B1 | 2/2003 | Bougamont et al. |
| 6,824,080 | B2 | 11/2004 | Matsugi et al. |
| 6,835,389 | B1 | 12/2004 | Dohi et al. |
| 6,906,027 | B2 | 6/2005 | Oki et al. |
| 7,278,982 | B2 | 10/2007 | Tsutsui |
| 7,306,787 | B2 | 12/2007 | Tarara et al. |
| 7,353,823 | B2 | 4/2008 | Tsutsui |
| 7,638,138 | B2 | 12/2009 | Oki et al. |
| 2001/0038824 | A1 | 11/2001 | Horii et al. |
| 2002/0002172 | A1 | 1/2002 | Bell-Huff et al. |
| 2002/0012688 | A1 | 1/2002 | Dohi et al. |
| 2002/0040139 | A1 | 4/2002 | Billotte et al. |

(Continued)

FOREIGN PATENT DOCUMENTS

EP        0122036 A1    10/1984

(Continued)

OTHER PUBLICATIONS

Merriam-Webster's Collegiate Dictionary, 10th edition, Merriam-Webster Incorporated: Springfield, Massachusetts, 1993, pp. 41.*
Hens et al., "BMP4 and PTHrP interact to stimulate ductal outgrowth during embryonic mammary development and to inhibit hair follicle induction," Development 2007, 234, pp. 1221-1230.*
"Fluorouracil" definition viewed on the National Cancer Institute website at www.cancer.gov/drugdictionary?cdrid=43130 on May 31, 2012.*
UK combined office action and search report dated Nov. 10, 2010 for Application No. GB1012959.1.

(Continued)

Primary Examiner — James H. Alstrum-Acevedo
(74) Attorney, Agent, or Firm — Wilson Sonsini Goodrich & Rosati

(57) ABSTRACT

Disclosed is a preparation for transnasal application, which has improved fluidability. Specifically disclosed is a preparation for transnasal application, which comprises at least a complex comprising: a fluidability-improving component comprising a first crystalline cellulose (A) having specified powder properties, tricalcium phosphate (B) having specified powder properties, and a second crystalline cellulose (C) having specified powder properties or a starch (D) having specified powder properties; and a physiologically active substance.

34 Claims, 17 Drawing Sheets

U.S. PATENT DOCUMENTS

| | | | |
|---|---|---|---|
| 2004/0063615 A1 | 4/2004 | Oki et al. | |
| 2004/0173211 A1 | 9/2004 | Kladders et al. | |
| 2005/0042177 A1 | 2/2005 | Ryde et al. | |
| 2005/0177095 A1 | 8/2005 | Tsutsui | |
| 2006/0106057 A1* | 5/2006 | Daniel et al. | 514/310 |
| 2006/0217658 A1 | 9/2006 | Tsutsui | |
| 2006/0233715 A1 | 10/2006 | Oki et al. | |
| 2007/0060868 A1 | 3/2007 | Tsutsui | |
| 2008/0127972 A1* | 6/2008 | Morton | 128/203.15 |
| 2008/0260848 A1 | 10/2008 | Nagata et al. | |
| 2008/0286362 A1* | 11/2008 | Baran, Jr. et al. | 424/489 |
| 2009/0169640 A1 | 7/2009 | Oki et al. | |
| 2010/0178331 A1 | 7/2010 | Nagata et al. | |
| 2011/0033544 A1 | 2/2011 | Nagata et al. | |
| 2011/0045088 A1 | 2/2011 | Tsutsui et al. | |

FOREIGN PATENT DOCUMENTS

| | | | |
|---|---|---|---|
| EP | 0761248 A1 | 3/1997 | |
| EP | 0943326 A1 | 9/1999 | |
| EP | 1025859 A1 | 8/2000 | |
| EP | 1108423 A1 | 6/2001 | |
| EP | 1454648 A1 | 9/2004 | |
| EP | 1504780 A1 | 2/2005 | |
| EP | 1785145 A1 | 5/2007 | |
| JP | 3912469 | 7/1964 | |
| JP | 53127553 | 11/1978 | |
| JP | 54062328 | 5/1979 | |
| JP | 60-224616 | 11/1985 | |
| JP | 62-42888 | 9/1987 | |
| JP | 63267731 | 11/1988 | |
| JP | 5-32560 | 2/1993 | |
| JP | 8-098888 | 4/1996 | |
| JP | 9-276405 | 10/1997 | |
| JP | 9-291026 A | 11/1997 | |
| JP | 11/216357 | 8/1999 | |
| JP | 2000-229859 A | 8/2000 | |
| JP | 2000-239187 | 9/2000 | |
| JP | 2002-255795 A | 9/2002 | |
| WO | WO 95/12399 A1 | 5/1995 | |
| WO | WO 95/34582 A1 | 12/1995 | |
| WO | WO 97/31626 A1 | 9/1997 | |
| WO | WO 99/16470 A1 | 8/1999 | |
| WO | WO 00/12063 A1 | 3/2000 | |
| WO | WO 00/12136 A1 | 3/2000 | |
| WO | WO 00/23023 A1 | 4/2000 | |
| WO | WO 02/094233 A1 | 11/2002 | |
| WO | WO 03/095008 A1 | 11/2003 | |
| WO | WO 2004/004922 A1 | 1/2004 | |
| WO | WO 2004/073729 A1 | 9/2004 | |
| WO | WO 2005/056008 A1 | 6/2005 | |
| WO | WO 2006/040680 A1 | 4/2006 | |
| WO | WO 2008/031028 A2 | 3/2008 | |
| WO | WO 2008/075102 A1 | 6/2008 | |
| WO | WO 2008/078730 A1 | 7/2008 | |
| WO | WO 2008/031028 A3 | 11/2008 | |

OTHER PUBLICATIONS

International search report (partial) dated Dec. 21, 2010 for PCT Application No. IB2010/02168.

U.S. Appl. No. 12/576,219, filed Oct. 8, 2009, Tsutsui et al.

International search report and written opinion dated Jun. 28, 2011 for PCT Application No. IB2010/02168.

Office action dated Sep. 28, 2011 for JP Application No. 2006-531575 (in Japanese with English translation).

UK search report dated Sep. 9, 2011 for Application No. GB1012959.1.

European search report dated Jul. 15, 2008 for Application No. 05768543.0.

International search report dated May 7, 2003 for PCT Application No. JP2003/001948.

International search report dated Nov. 1, 2005 for PCT Application No. JP2005/014389.

International search report Jun. 8, 2010 for PCT Application No. JP2010/003285.

Kleinebudde, et al. Influence of degree of polymerization on behavior of cellulose during homogenization and extrusion/spheronization. AAPS Pharmasci 2000, 2(2) Article 21, 1-10.

Rowe, et al (Eds). Handbook of Pharmaceutical Excipients. Pharmaceutical Press. 2003. p. 108-109.

European search report and opinion dated Dec. 19, 2011 for Application No. 07860016.0.

International search report dated Feb. 5, 2008 for PCT Application. No. JP2007/074787.

* cited by examiner

US 8,337,817 B2

PREPARATION FOR TRANSNASAL APPLICATION

TECHNICAL FIELD

The present invention relates to nasal preparations. Specifically, the present invention relates to nasal preparations that enable high nasal drug absorption and have improved flowability for efficient productivity.

BACKGROUND ART

Nasal administration of drugs has long been commonly used as a method for administering drugs with local effects such as in rhinitis treatments. However, nasal administration has also drawn attention as an administration route for drugs with systemic effects, for example, peptide/protein drugs such as insulin and calcitonin, and low molecular-weight drugs such as morphine. The reasons include the facts that nasal mucosa has well-developed vascular plexus and is histologically advantageous for drug absorption, drugs absorbed through nasal mucosa can avoid first-pass metabolism in the gastrointestinal tract and liver, and self administration is easy and painless.

Methods for nasal drug administration include, for example, methods in which a drug is dissolved and the resulting liquid or suspension is administered and methods in which a drug is administered as a powdery preparation. In the market, nasal drugs in liquid form are more common than powdery nasal preparations. However, Ishikawa et al. have reported that powdery preparations are superior to liquid preparations in drug retention in a nasal cavity and thus show improved nasal drug absorption (Non-Patent Document 1). The same tendency has also been observed in the present inventors' studies. Also, in order to nasally administer a powdery drug preparation and achieve effective absorption and drug efficacy, it is preferable to administer the preparation in combination with a carrier. Many effective carriers have been reported. For example, divalent metal ions such as calcium with an average particle diameter of 250 μm or less have been disclosed as carriers for nasal administration (Patent Document 1).

Also, according to a report (Patent Document 3), nasal drug absorption of a formulation containing water-absorbing and water-insoluble base such as crystalline cellulose was improved by combining it with a water-absorbing and gel-forming base such as hydroxypropyl cellulose, in comparison with a formulation containing crystalline cellulose alone (Patent Document 2). Meanwhile, the present inventors have reported that when used alone, crystalline cellulose of a particular particle size distribution enables efficient absorption of drugs, such as insulin, through nasal mucosa (Patent Documents 4, 5, and 6).

Generally, required amounts of said effective powdery nasal preparations are delivered into the nasal cavity by methods, such as those that use a single-dose nasal administration device or the like utilizing capsules or blister packs which are filled by an automatic filling machine (Patent Documents 7 and 8) or those that use a multiple-dose nasal administration device or the like containing a drug reservoir filled with the preparation and, at the time of use, a single dose amount is measured from the reservoir and dispensed in a small chamber and delivered into the nasal cavity (Patent Document 9). Non-Patent Document 1: International Journal of Pharmaceutics, 224, 105-114, 2001

Patent Document 1: Japanese Patent Application Kokai Publication No. (JP-A) H08-27031 (unexamined, published Japanese patent application)
Patent Document 2: JP-A (Kokai) S59-163313
Patent Document 3: JP-A (Kokai) H10-59841
Patent Document 4: International Patent Application Publication WO 03-004048 pamphlet
Patent Document 5: JP-A (Kokai) 2003-206227
Patent Document 6: International Patent Application Publication WO 2006/016530 pamphlet
Patent Document 7: JP-A (Kokai) H08-206208
Patent Document 8: JP-A (Kokai) 2003-154006
Patent Document 9: JP-A (Kokai) 2003-175103

DISCLOSURE OF THE INVENTION

Problems to be Solved by the Invention

To improve productivity in the methods described above, it is necessary to be able to fill a pre-determined amount of powdery preparation into capsules with ease and high accuracy, or to dispense a pre-determined amount of powdery preparation with ease and high accuracy within a device. Thus, among the powder properties of powdery preparations, there is a need for high flowability.

Various effective carriers of nasal administration for improving nasal drug absorption have been reported. One of such useful carriers for nasal administration is crystalline cellulose with a particular particle size distribution reported by the present inventors in International Patent Application Publication WO 03-004048 pamphlet, JP-A (Kokai) 2003-206227, and International Patent Application Publication WO 2006/016530 pamphlet.

However, the flowability of conventional crystalline cellulose is poor, and thus it is still industrially problematic considering the manufacturing efficiency associated with the process of capsule filling by automated machines and the spraying efficiency of nasal devices.

In general, to fill capsules or blister packs with a pre-determined amount of powdery preparation, an automated process must fill measuring cavities with a pre-determined amount of powdery preparation. In this filling process, because the flowability of a powdery preparation significantly affects the uniformity in the filling amount, having adequate flowability for the filling system is important for the quality of the filling, such as the variability in the amount, and stability in the filling process.

Meanwhile, powdery nasal preparations need to be delivered into a nasal cavity from a capsule or blister pack by air flow generated by pressing the pump component of a nasal device. Since powdery preparations with poor flowability tend to remain in the preparation channel of a capsule or device, an adequate dose cannot be delivered into a nasal cavity and thus sometimes the expected therapeutic effect cannot be produced.

Improving the flowability of a powdery preparation is usually attempted to solve these various flowability-associated problems. The most common method for improving the flowability of powdery preparations is adding lubricants such as magnesium stearate, or fluidizing agents such as talc and silicon dioxide. Such lubricants and fluidizing agents are thought to reduce the friction and adhesion among powder particles by adhering onto the powder surface and increasing the space among the particles and, as a result, produce the flowability-improving effect.

Previously, the present inventors added the lubricants and fluidizing agents described above in an attempt to improve the poor flowability of crystalline cellulose which is useful as a carrier for nasal administration, but failed to improve the flowability to a satisfactory level.

Thus, an objective of the present invention is to provide carriers and preparations with improved flowability, which deeply affects productivity in the process of automated capsule filling and issues related to a device's spray efficiency, by using a specific crystalline cellulose which is useful as a carrier of nasal administration and previously provided by the present inventors (hereinafter referred to as "first crystalline cellulose") (WO 03-004048, JP-A (Kokai) 2003-206227, and WO 2006/016530).

Another important objective is to improve the flowability using methods that have no influence on the effect of the crystalline cellulose to increase nasal drug absorption.

Means for Solving the Problems

To achieve the above-described objectives, the present inventors conducted dedicated studies on carriers that have improved flowability without affecting nasal drug absorption. As a result, the present inventors discovered that preparations containing a physiologically active substance and a powder flowability-improving component, obtained by combining a first crystalline cellulose with tribasic calcium phosphate and another particular crystalline cellulose (a second crystalline cellulose) or starch, had superior flowability, and the present inventors completed the present invention. Specifically, the present invention includes:

[1] a nasal preparation, which comprises at least a complex of a physiologically active substance and a powder flowability-improving component comprising:
crystalline cellulose (A), which is a first crystalline cellulose with an untapped bulk density of 0.13 to 0.29 g/cm$^3$, a specific surface area of 1.3 m$^2$/g or more, an average particle diameter of 30 μm or less, and an angle of repose of 55° or more;
tribasic calcium phosphate (B); and
crystalline cellulose (C), which is a second crystalline cellulose with an untapped bulk density of 0.26 to 0.48 g/cm$^3$, a specific surface area of 1.3 m$^2$/g or less, an angle of repose of 50° or less, and an average particle diameter of 150 μm or less, or starch (D) with an untapped bulk density of 0.35 to 0.65 g/cm$^3$, a specific surface area of 1.3 m$^2$/g or less, an angle of repose of 55° or less, and an average particle diameter of 150 μm or less;
wherein the flowability-improving component comprises 0.1 to 10 (W/W) % tribasic calcium phosphate (B), 5.0 to 30 (W/W) % second crystalline cellulose (C) and/or starch (D), and the remainder is the first crystalline cellulose (A); and
the nasal preparation comprises the physiologically active substance at a weight ratio of 0.0001 to 1.2 in its free form without being converted to the salt form, when the total weight of the flowability-improving component is taken as 1;

[2] a nasal preparation, which comprises at least a complex of a physiologically active substance and a powder flowability-improving component comprising:
crystalline cellulose (A), which is a first crystalline cellulose with an untapped bulk density of 0.13 to 0.29 g/cm$^3$, a specific surface area of 1.3 m$^2$/g or more, an average particle diameter of 30 μm or less, and an angle of repose of 55° or more;
tribasic calcium phosphate (B); and
crystalline cellulose (C), which is a second crystalline cellulose with an untapped bulk density of 0.26 to 0.48 g/cm$^3$, a specific surface area of 1.3 m$^2$/g or less, an angle of repose of 50° or less, an average particle diameter of 150 μm, or less, or starch (D) with an untapped bulk density of 0.35 to 0.65 g/cm$^3$, a specific surface area of 1.3 m$^2$/g or less, an angle of repose of 55° or less, an average particle diameter of 150 μm or less;
wherein the flowability-improving component comprises 0.1 to 10 (W/W) % tribasic calcium phosphate (B), 5.0 to 30 (W/W) % second crystalline cellulose (C) and/or starch (D), and the remainder is the first crystalline cellulose (A);
and the nasal preparation is produced by applying a shearing force to the first crystalline cellulose (A), tribasic calcium phosphate (B), second crystalline cellulose (C) or starch (D), and physiologically active substance, and mixing the physiologically active substance at a weight ratio of 0.0001 to 1.2 in its free form without being converted to the salt form, when the total weight of the flowability-improving component is taken as 1;

[3] the nasal preparation of [1] or [2], wherein the second crystalline cellulose (C) has an untapped bulk density of 0.35 to 0.46 g/cm$^3$, a specific surface area of 1.0 m$^2$/g or less, an angle of repose of 45° or less, and a average particle diameter of 75 μm or less;

[4] the nasal preparation of any one of [1] to [3], wherein the average particle diameter of tribasic calcium phosphate (B) is 100 μm or less;

[5] the nasal preparation of any one of [1] to [4], wherein the angle of repose is 53° or less;

[6] the nasal preparation of any one of [1] to [5], wherein the physiologically active substance is a peptide/protein drug and/or a non-peptide/non-protein drug including a low-molecular-weight drug;

[7] the nasal preparation of [6], wherein the peptide/protein drug is at least one selected from the group consisting of insulin, growth hormone, growth hormone releasing peptide, ghrelin, glucagon, calcitonin, interferon, erythropoietin, interleukin, PTH(1-84), PTH(1-34), PTH-related peptides, GLP-1, vasopressin, leuprorelin, granulocyte-colony stimulating factor, prolactin, human menopausal gonadotropin, chorionic gonadotropin, follicle stimulating hormone, luteinizing hormone, leptin, nerve growth factor (NGF), stem cell growth factor (SCGF), keratinocyte growth factor (KGF), thioredoxin, cyclosporin, influenza vaccine, and analogs thereof;

[8] the nasal preparation of [6], wherein the non-peptide/non-protein drug including a low-molecular-weight drug is at least one selected from the group consisting of morphine, fentanyl, oxycodone, butorphanol, tramadol, granisetron, ondansetron, tropisetron, palonosetron, indisetron, sumatriptan, zolmitriptan, rizatriptan, naratriptan, ergotamine, triazolam, melatonin, carbamazepine, midazolam, donepezil, tiapride, cefaclor, enoxacin, aciclovir, zidvudine, didanosine, nevirapine, indinavir, dantrolene, digoxin, trihexyphenidyl, biperiden, dextromethorphan, naloxone, betahistine, naphazoline, diltiazem, tranilast, loperamide, diclofenac, beclomethasone, chlorpheniramine, sildenafil, vardenafil, cyanocobalamin, finasteride, epinephrine, 5-fluorouracil (5-FU), low-molecular-weight heparin, tacrolimus, RNA, RNAi, siRNA, antisense DNA, and allergen extract powder; and

[9] the nasal preparation of any one of [1] to [8], which further comprises a pH adjustor, preservative, stabilizer, flavor, absorbefacient, or substance that captures a divalent calcium ion.

The nasal preparations of the present invention comprise at least one complex of a physiologically active substance and a flowability-improving component.

Herein, the "powder flowability-improving component" refers to a component that is added to improve the flowability of nasal preparations of the invention of the present application. Such flowability-improving components include, for example, crystalline cellulose having particular powder properties, tribasic calcium phosphate, and starch.

Herein, the "physiologically active substance" is not particularly limited, and includes drugs having systemic or local effects, drugs for enhancing biological defense function, drugs that target the brain, and peptide/protein drugs and non-peptide/non-protein drugs including low-molecular-weight drugs. The substance is not also limited by the type of derivatives, salts, or the like.

Specifically, such peptide/protein drugs include, for example, insulin, growth hormone, growth hormone releasing peptide, ghrelin, glucagon, calcitonin, interferon, erythropoietin, interleukin, PTH(1-84), PTH(1-34), PTH-related peptides, GLP-1, vasopressin, leuprorelin, granulocyte-colony stimulating factor, prolactin, human menopausal gonadotropin, chorionic gonadotropin, follicle stimulating hormone, luteinizing hormone, leptin, nerve growth factor (NGF), stem cell growth factor (SCGF), keratinocyte growth factor (KGF), thioredoxin, cyclosporin, influenza vaccine, and analogs thereof. Of these, preferred peptide/protein drugs are insulin, PTH(1-34), and human menopausal gonadotropin.

Specifically, the low-molecular-weight drugs include, for example, analgesic agents such as morphine, fentanyl, oxycodone, butorphanol, and tramadol; antiemetic agents such as granisetron, ondansetron, tropisetron, palonosetron, and indisetron; antimigraine agents such as sumatriptan, zolmitriptan, rizatriptan, naratriptan, and ergotamine; sleep-inducing agents such as triazolam and melatonin; anticonvulsants such as carbamazepine; sedatives such as midazolam; antidementia agents such as donepezil; brain activators such as tiapride; antibiotics such as cefaclor; antibacterial agents such as enoxacin; antiviral agents such as aciclovir, zidvudine, didanosine, nevirapine, and indinavir; muscle relaxants such as dantrolene; cardiac stimulants such as digoxin; therapeutic agents for Parkinson's disease such as trihexyphenidyl and biperiden; antitussive agents and expectorants such as dextromethorphan; respiratory stimulants such as naloxone; antidinic agents such as betahistine; angiotonic agents such as naphazoline; coronary vasodilators such as diltiazem; therapeutic agents for asthma such as tranilast; antidiarrheal agents such as loperamide; NSAIDs such as diclofenac; steroids such as beclomethasone; antihistamic agents such as chlorpheniramine; agents for improvement in sexual function such as sildenafil and vardenafil; vitamins such as cyanocobalamin; hair growing agents such as finasteride; antianaphylactic agents such as epinephrine; and antitumor agents such as 5-FU. Of these low-molecular-weight drugs, preferred drugs are morphine, granisetron, ondansetron, fentanyl, oxycodone, sumatriptan, zolmitriptan, beclomethasone, and ketotifen.

In addition to the above examples, the low-molecular-weight drugs also include antithrombotic agents such as low-molecular-weight heparin; tacrolimus; RNA; RNAi; siRNA; antisense DNA; and allergen extract powder which is used in hyposensitization treatments for pollinosis.

The ratio of physiologically active substance added in the nasal preparations of the present application depends on the type of physiologically active substance. The physiologically active substance is added at a weight ratio of preferably 0.0001 to 1.2, more preferably 0.01 to 0.6 in its free form without being converted to the salt form, when the total weight of the flowability-improving component is taken as 1.

The present invention comprises the use of tribasic calcium phosphate to improve the flowability of a first crystalline cellulose, and the use of a specific second crystalline cellulose or starch to synergistically enhance the flowability-improving effect of the tribasic calcium phosphate.

The flowability-improving effect provided by the present invention is not obtained when magnesium stearate or talc, both of which are commonly used as a lubricant or fluidizing agent, is used instead of tribasic calcium phosphate. Thus, the present invention is highly unique.

BRIEF DESCRIPTION OF THE DRAWINGS

FIG. 1-2 shows the angles of repose when a fluidizing agent was added alone or added simultaneously with a flowability-enhancing agent (cornstarch) to Ceolus® PH-F20JP. In this diagram, "St-Mg" indicates magnesium stearate; "TALC" indicates talc; "TCP" indicates tribasic calcium phosphate; "PH-F20JP" indicates Ceolus® PH-F20JP; and "STARCH" indicates cornstarch.

FIG. 2 shows the angles of repose when 1% tribasic calcium phosphate as a fluidizing agent and Ceolus® PH-101, Ceolus® PH-102, Ceolus® PH-301, Ceolus® PH-302, or cornstarch as a flowability-enhancing agent were added at various ratios to Ceolus® PH-F20JP. In this graph, "TCP" indicates tribasic calcium phosphate; "PH-101" indicates Ceolus® PH-101; "PH-102" indicates Ceolus® PH-102; "PH-301" indicates Ceolus® PH-301; "PH-302" indicates Ceolus® PH-302; and "STARCH" indicates cornstarch.

FIG. 3-1 shows the angles of repose when tribasic calcium phosphate, magnesium stearate, or talc was added to Ceolus® PH-F20JP as a fluidizing agent at various ratios in combination with 10% Ceolus® PH-301 as a flowability-enhancing agent. In these graphs, "St-Mg" indicates magnesium stearate; "TALC" indicates talc; "TCP" indicates tribasic calcium phosphate; and "PH-301" indicates Ceolus® PH-301.

FIG. 3-2 shows the angles of repose when tribasic calcium phosphate, magnesium stearate, or talc was added to Ceolus® PH-F20JP as a fluidizing agent at various ratios in combination with 10% cornstarch as a flowability-enhancing agent. In these graphs, "St-Mg" indicates magnesium stearate; "TALC" indicates talc; TCP indicates tribasic calcium phosphate; and "STARCH" indicates cornstarch.

FIG. 5 shows the relationship between the angle of repose and variation in the filling amount (standard deviation when the average filling amount is taken as standard) when 50 capsules (gelatin, size 1) were filled with various compounding agents. The various compounding agents used in the assessment include: fluidizing agents added alone to Ceolus® PH-F20JP, and fluidizing agents and flowability-enhancing agents added simultaneously to Ceolus® PH-F20JP. In these graphs, "St-Mg" indicates magnesium stearate; "TALC" indicates talc; "TCP" indicates tribasic calcium phosphate; "PH-F20JP" indicates Ceolus® PH-F20JP; "PH-301" indicates Ceolus® PH-301; and "STARCH" indicates cornstarch.

Figure 6:
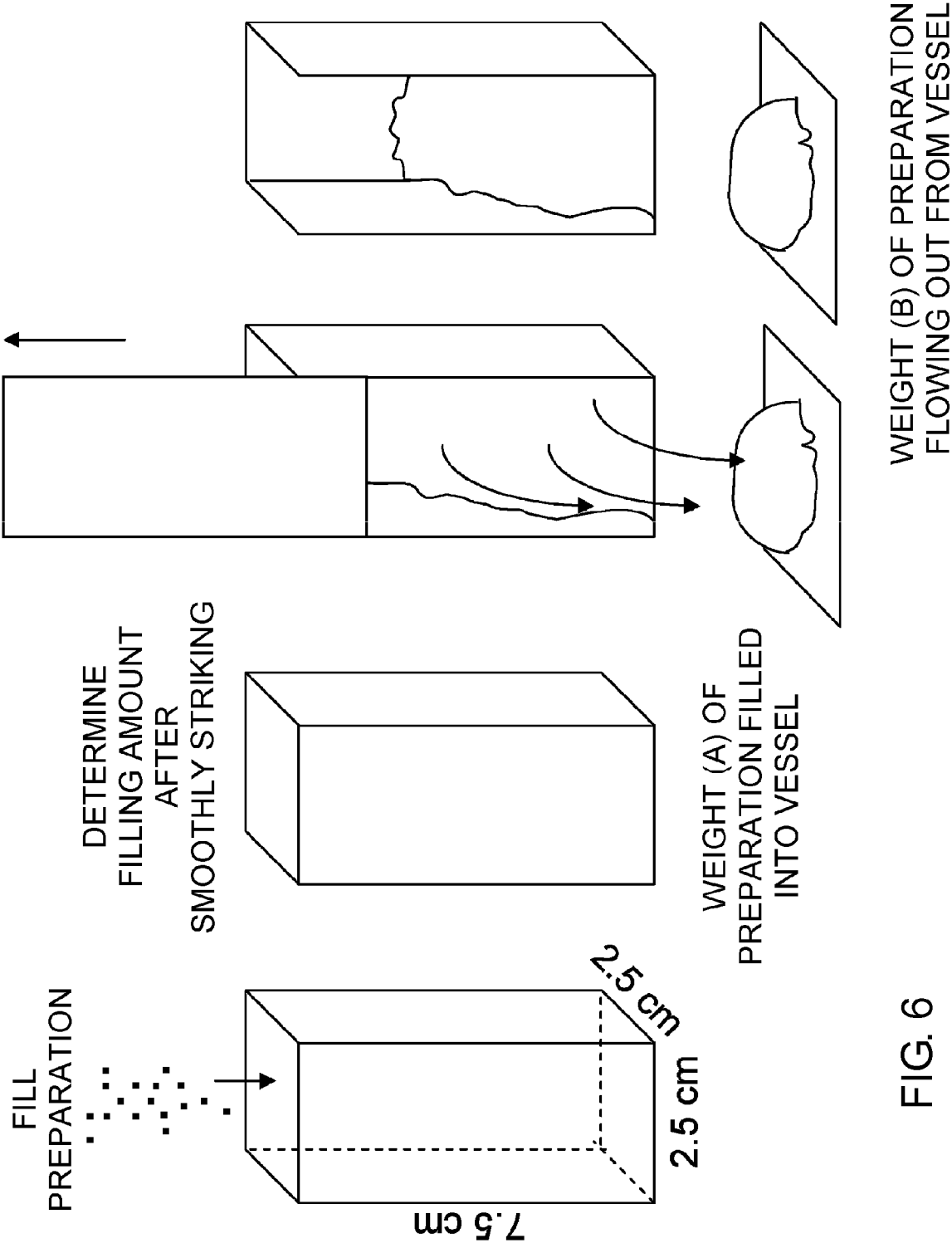

FIG. 6 is a diagram showing the procedure of collapse-slide test of carriers for nasal administration.

Figure 1:
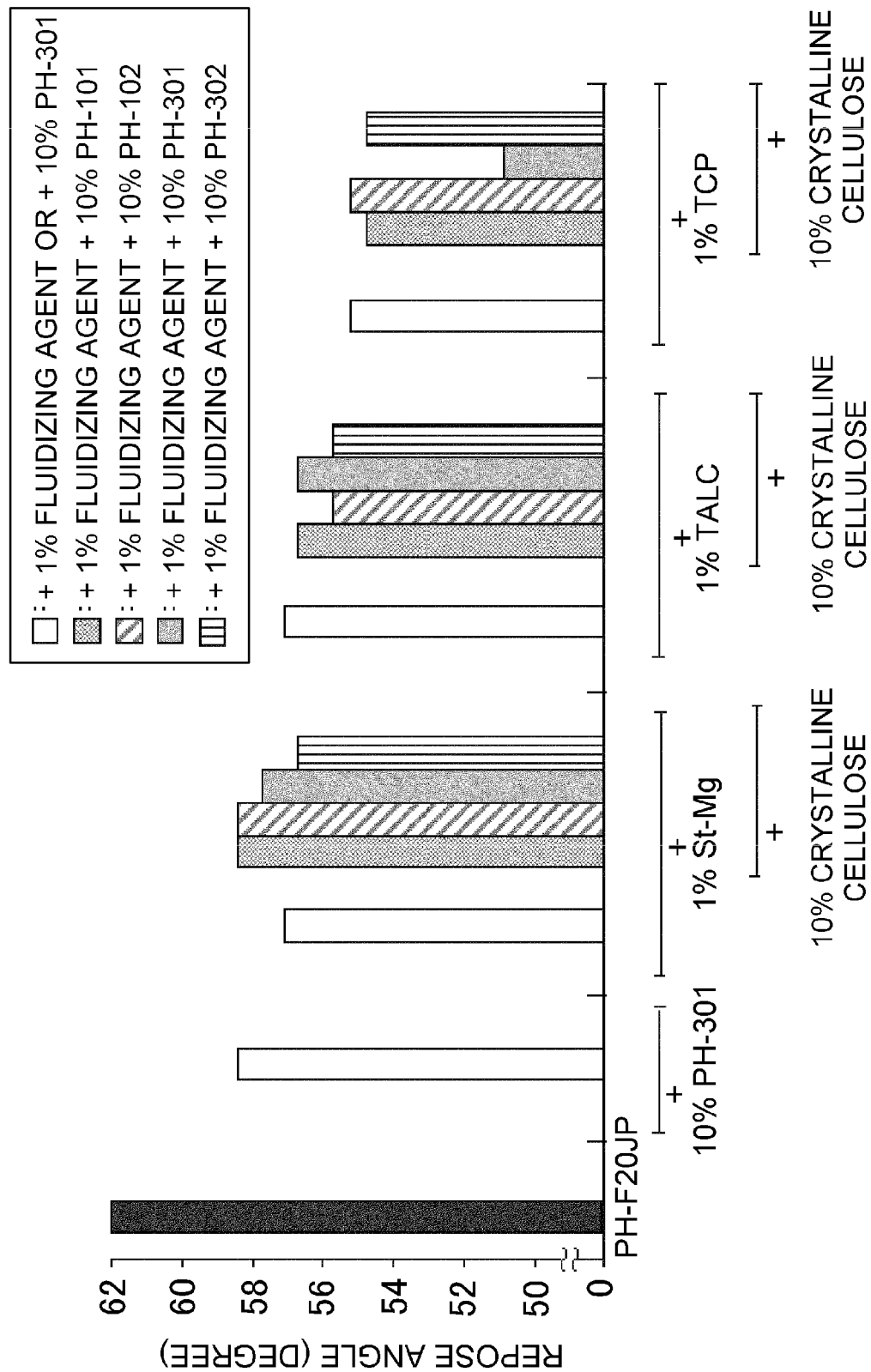
FIG. 1-1 shows the angles of repose when a fluidizing agent was added alone or added simultaneously with a flowability-enhancing agent (crystalline cellulose) to Ceolus® PH-F20JP. In this diagram, "St-Mg" indicates magnesium stearate; "TALC" indicates talc; "TCP" indicates tribasic calcium phosphate; "PH-F20JP" indicates Ceolus® PH-F20JP; "PH-101" indicates Ceolus® PH-101; "PH-102" indicates Ceolus® PH-102; "PH-301" indicates Ceolus® PH-301; and "PH-302" indicates Ceolus® PH-302.
Figures 1, 7:
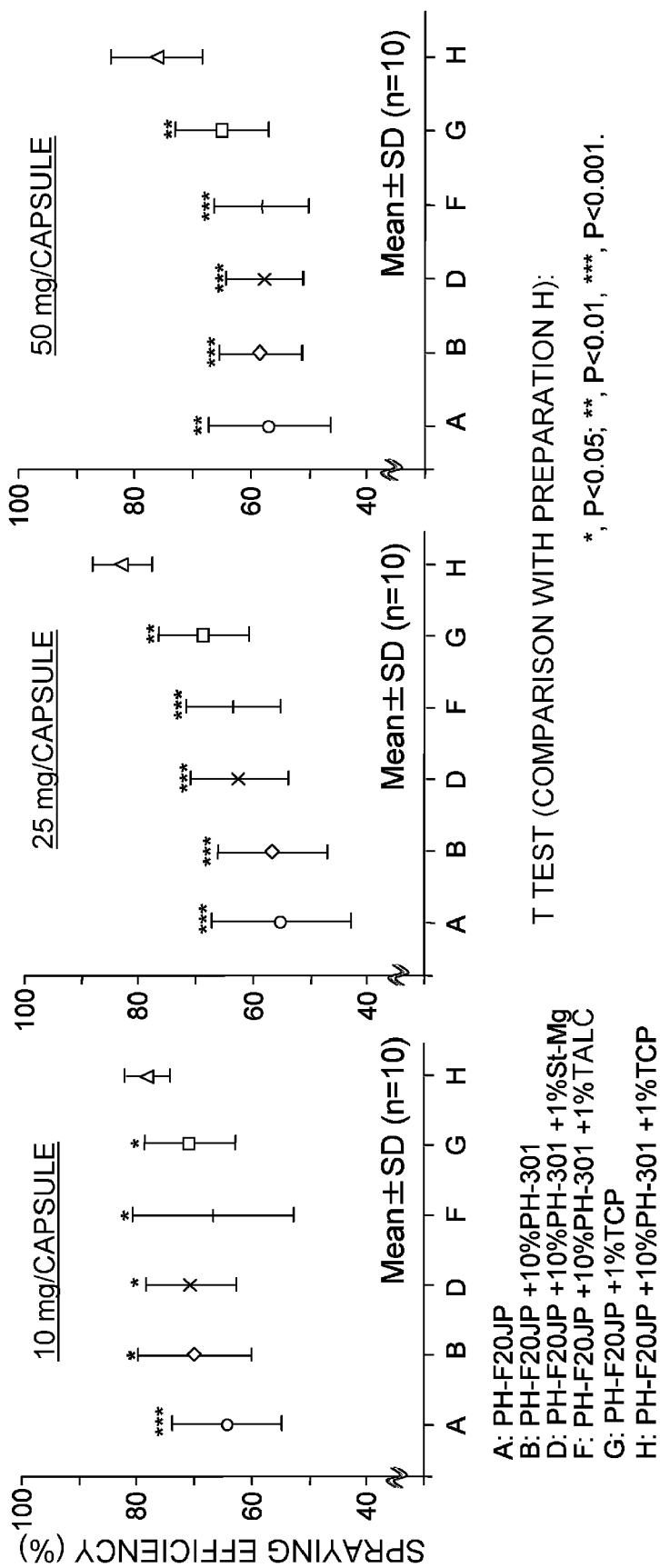
Figures 2, 7:
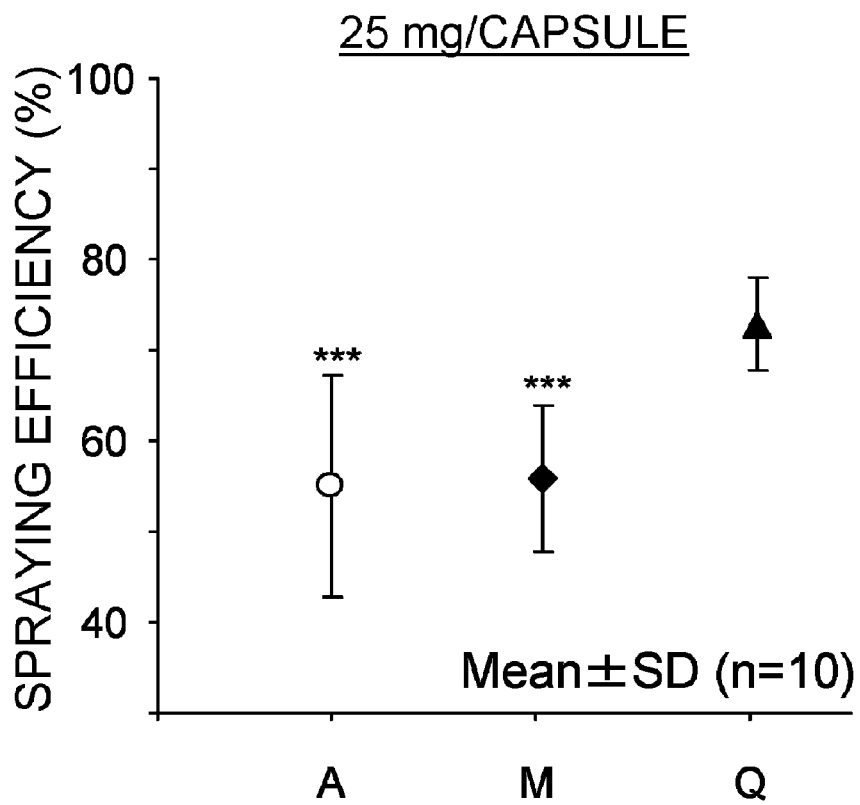

FIG. 7-1 shows the spray efficiency (%) of a nasal device (Publizer) for various compounding agents. The various compounding agents used in the assessment include:

fluidizing agents added alone to Ceolus® PH-F20JP, and fluidizing agents and flowability-enhancing agent (crystalline cellulose) added simultaneously to Ceolus® PH-F20JP. In these diagrams, "St-Mg" indicates magnesium stearate; "TALC" indicates talc; "TCP" indicates tribasic calcium phosphate; "PH-F20JP" indicates Ceolus® PH-F20JP; and "PH-301" indicates Ceolus® PH-301.

Figures 1, 2:
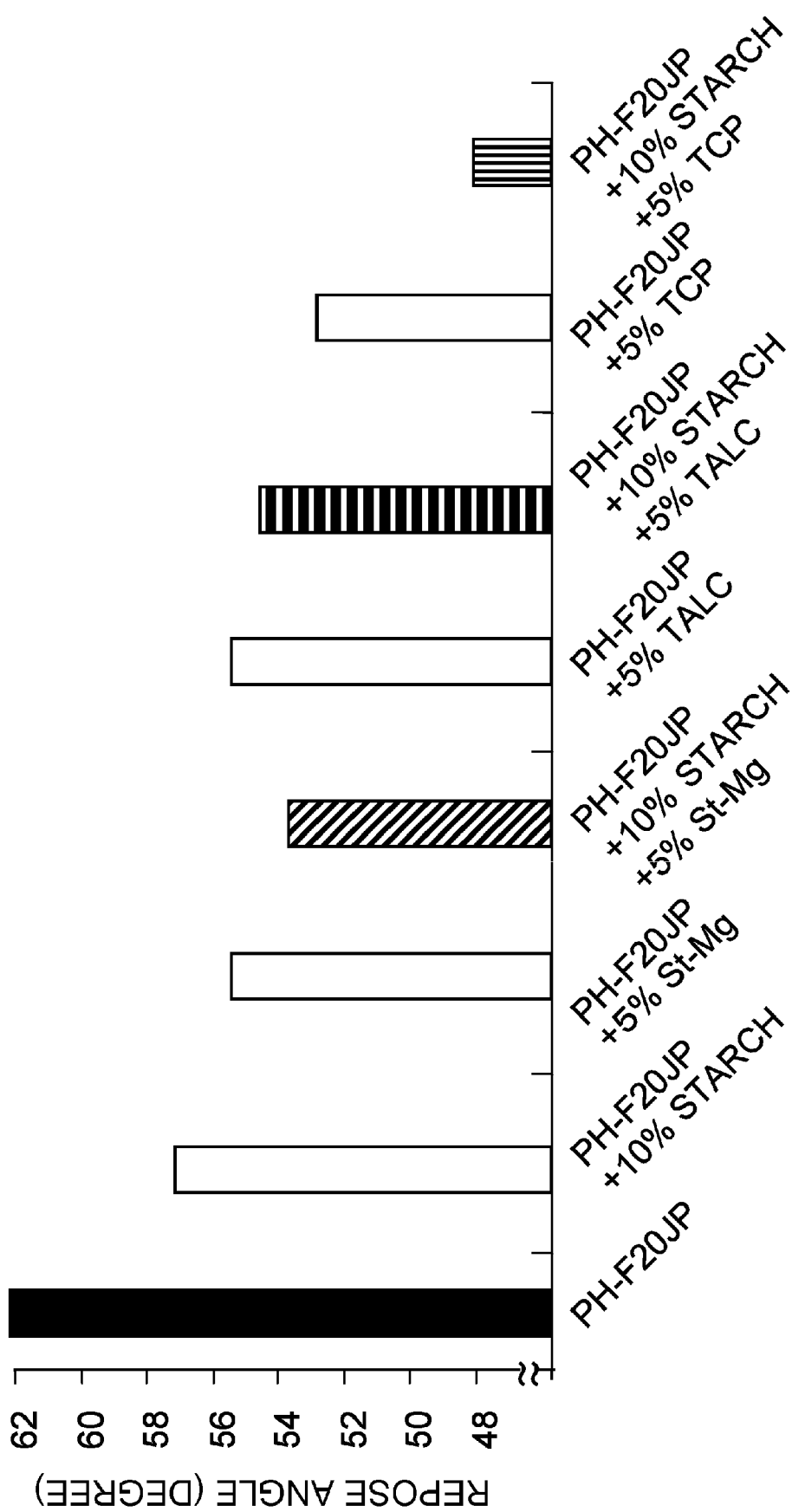
Figure 2:
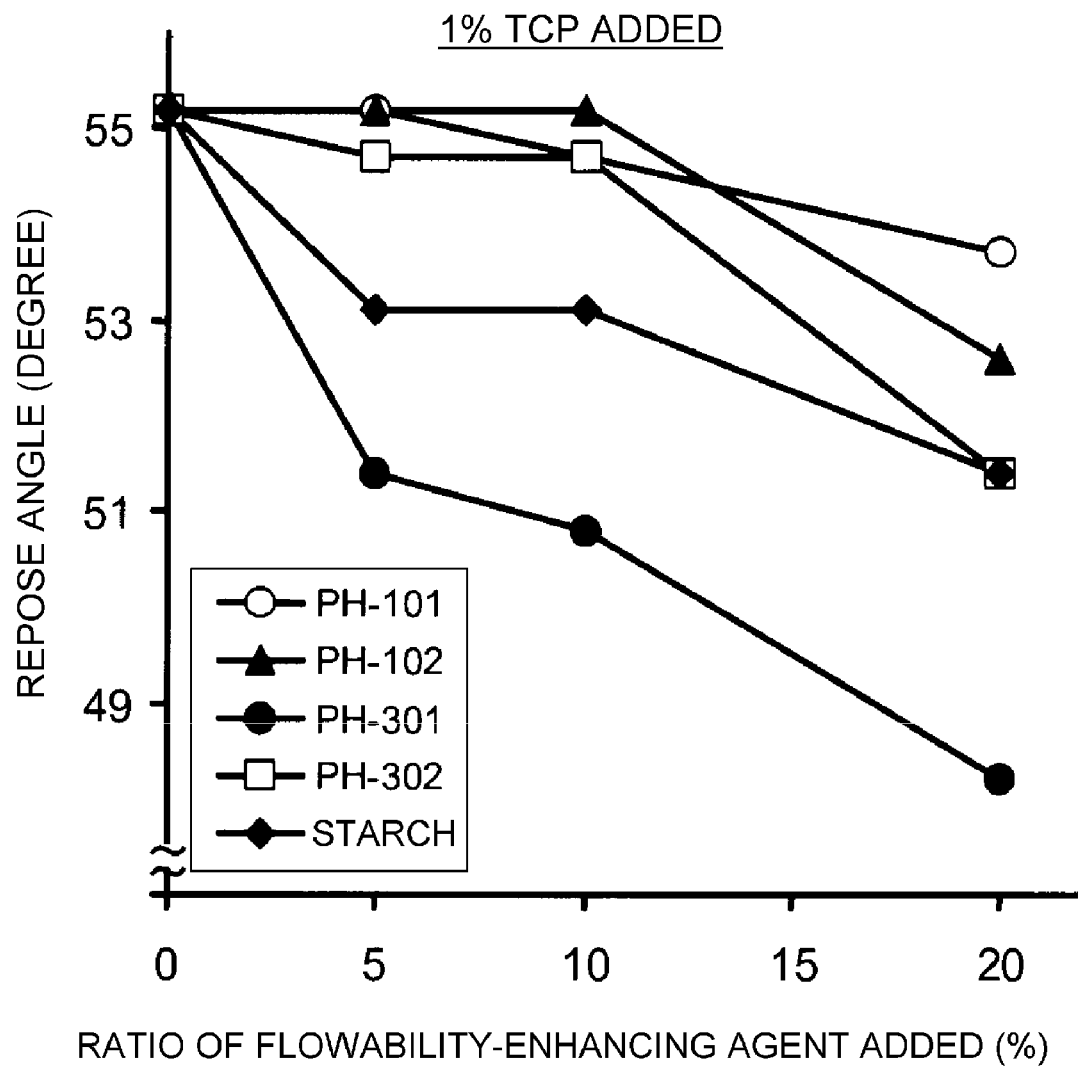

FIG. 7-2 is a diagram showing the spray efficiency (%) of a nasal device (Publizer) for various compounding agents. The various compounding agents used in the assessment include: a flowability-enhancing agent (cornstarch) added alone to Ceolus® PH-F20JP, and fluidizing agent (tribasic calcium phosphate) and flowability-enhancing agent (cornstarch) added simultaneously to Ceolus® PH-F20JP. In this diagram, "TCP" indicates tribasic calcium phosphate; "PH-F20JP" indicates Ceolus® PH-F20JP; and "STARCH" indicates cornstarch.

Figure 8:
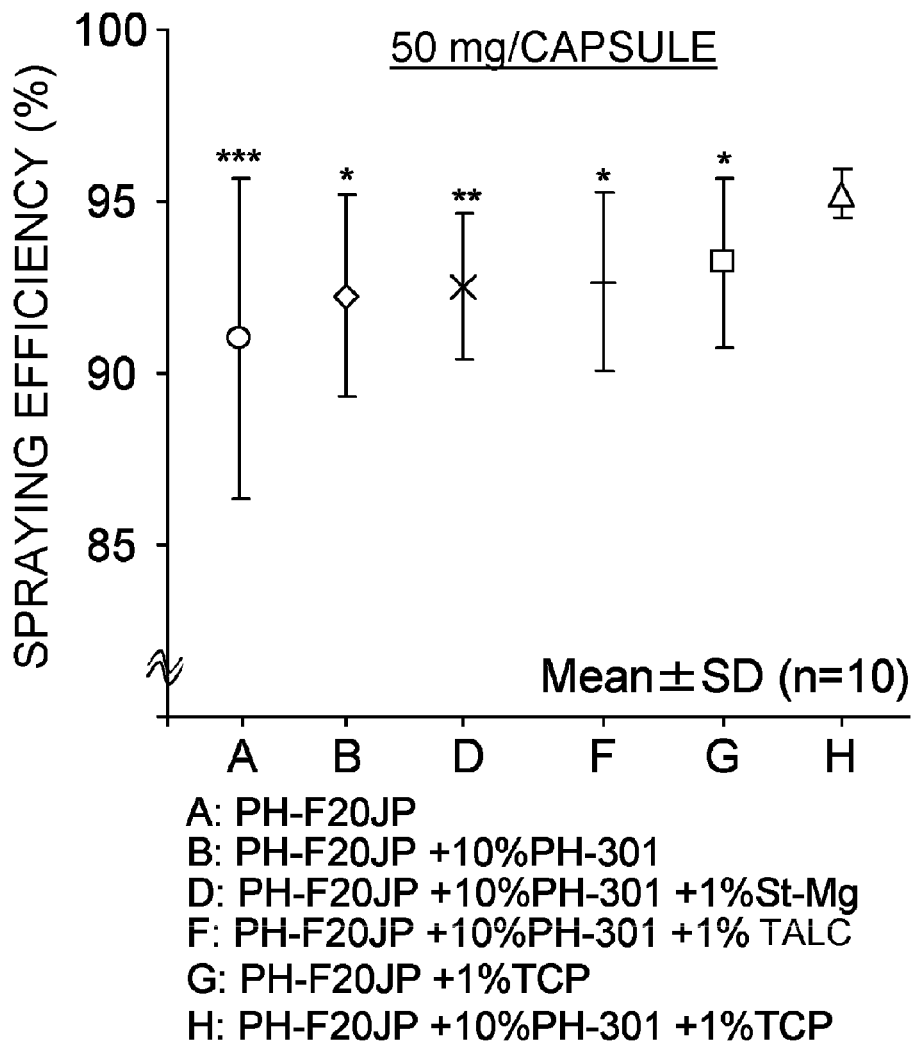

FIG. 8 is a diagram showing the spray efficiency (%) of a nasal device (Fit-lizer®) for various compounding agents. The various compounding agents used in the assessment include: fluidizing agents added alone to Ceolus® PH-F20JP, and fluidizing agents and flowability-enhancing agent (crystalline cellulose) added simultaneously to Ceolus® PH-F20JP. In this diagram, "St-Mg" indicates magnesium stearate; "TALC" indicates talc; "TCP" indicates tribasic calcium phosphate; "PH-F20JP" indicates Ceolus® PH-F20JP; and "PH-301" indicates Ceolus® PH-301.

Figure 9:
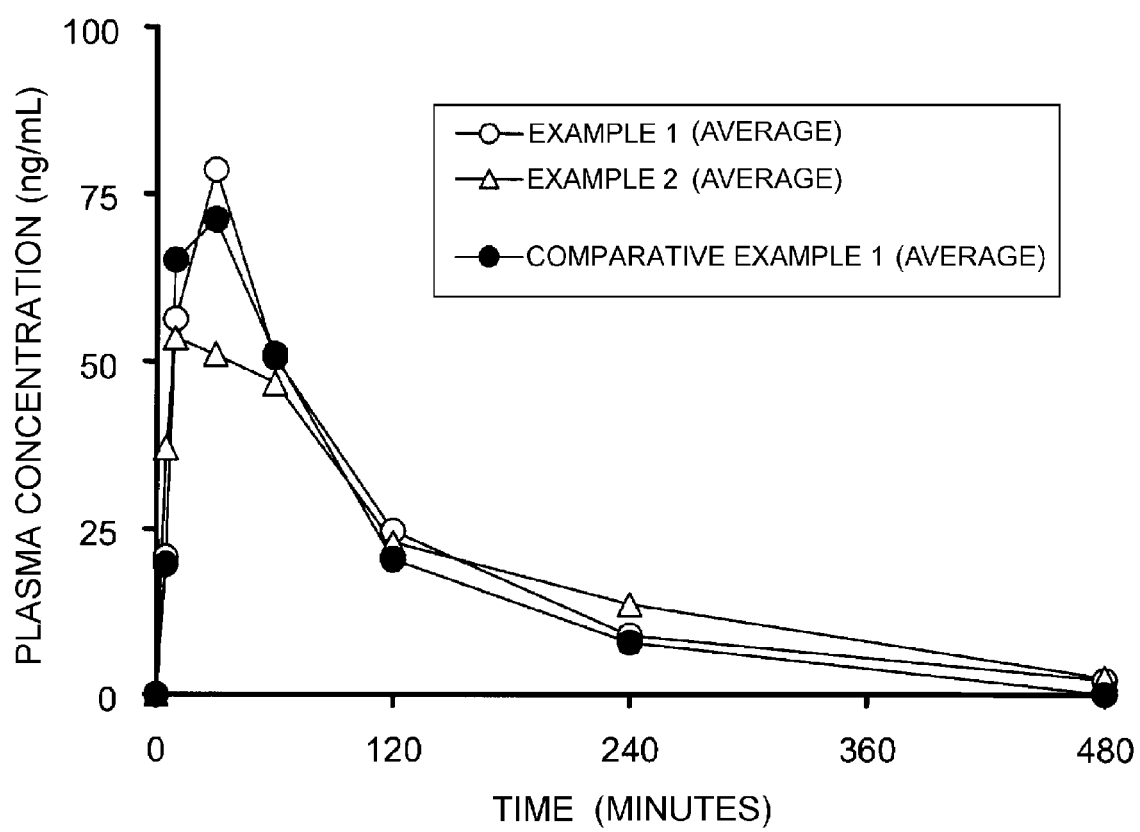

FIG. 9 is a graph showing the time course of plasma granisetron concentration after nasal administration of a nasal granisetron preparation to the monkeys.

Figure 10:
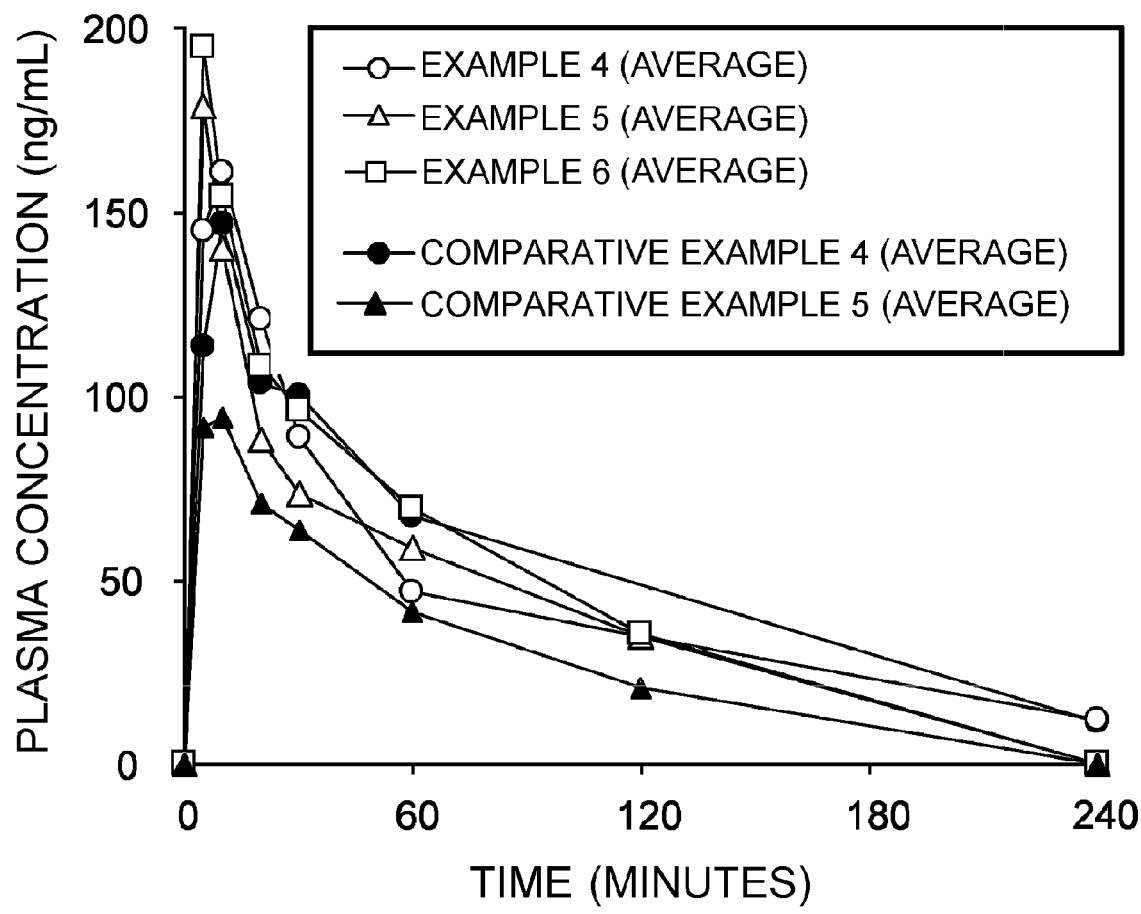

FIG. 10 is a graph showing the time course of plasma morphine concentration after administration of a nasal morphine preparation to the monkeys.

Figure 11:
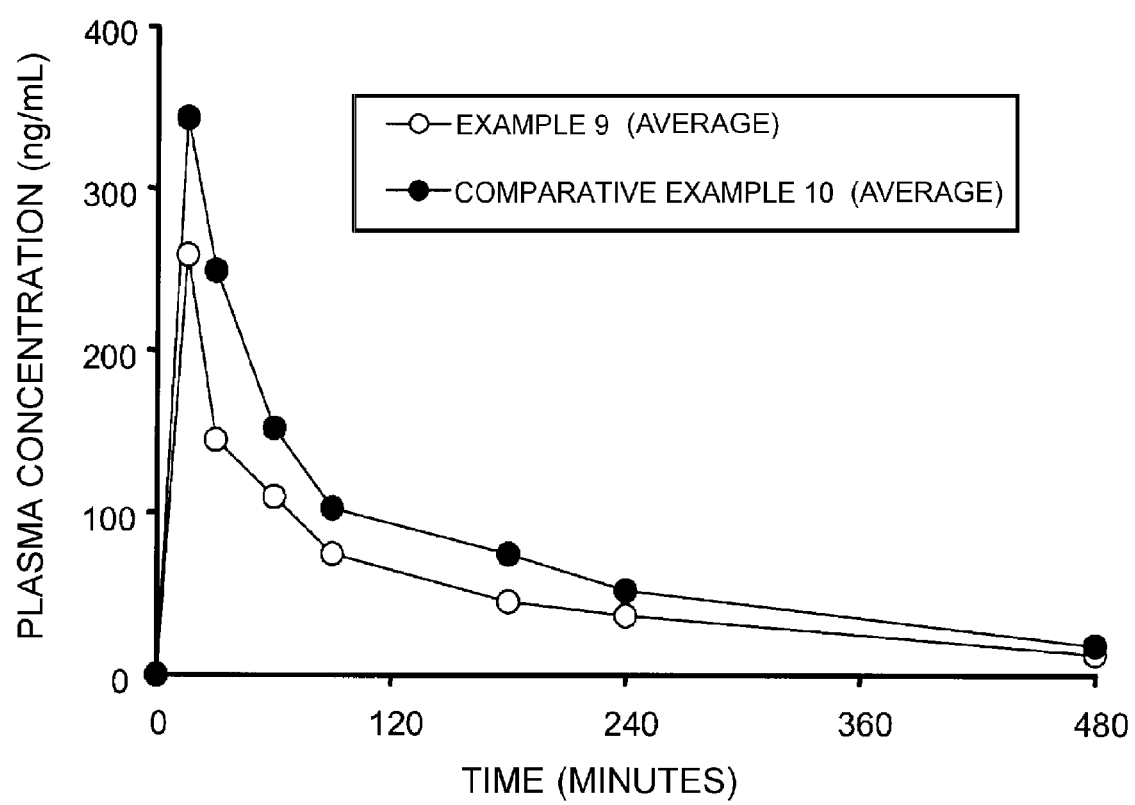

FIG. 11 is a graph showing the time course of plasma sumatriptan concentration after administration of a nasal sumatriptan preparation to the monkeys.

Figure 12:
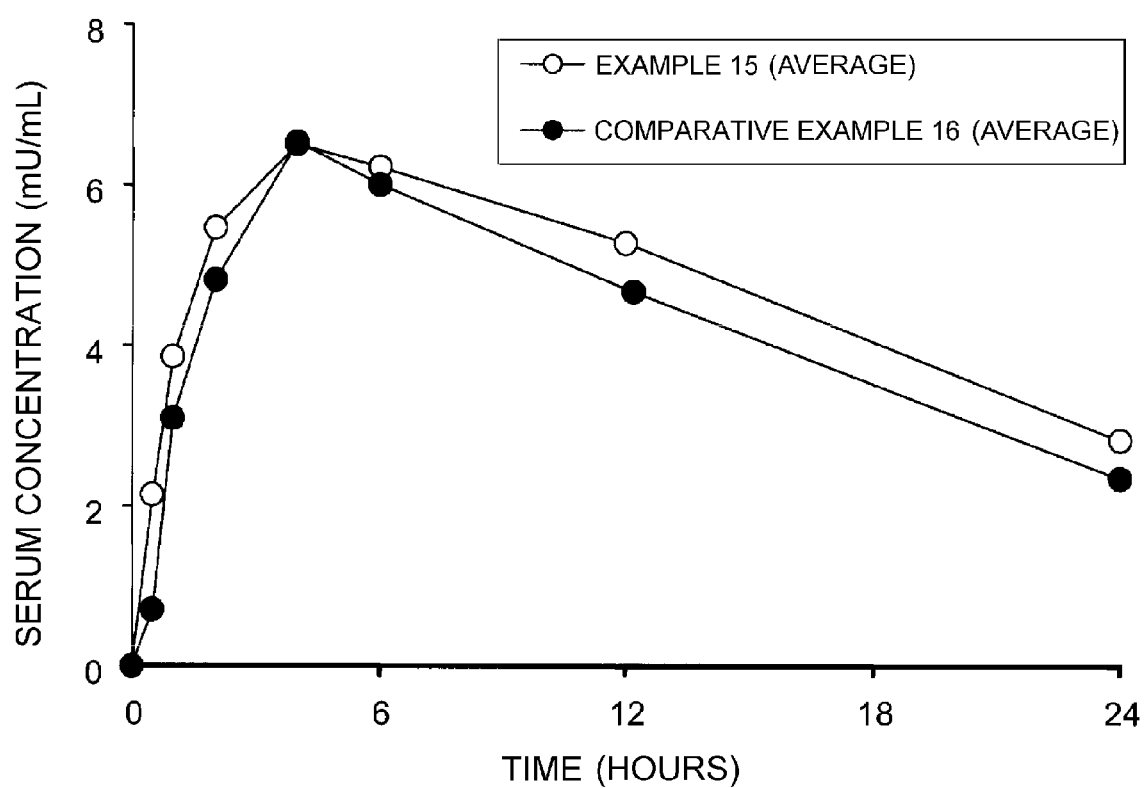

FIG. 12 is a graph showing the time course of serum FSH concentration after administration of a nasal HMG preparation to the monkeys.

Figure 13:
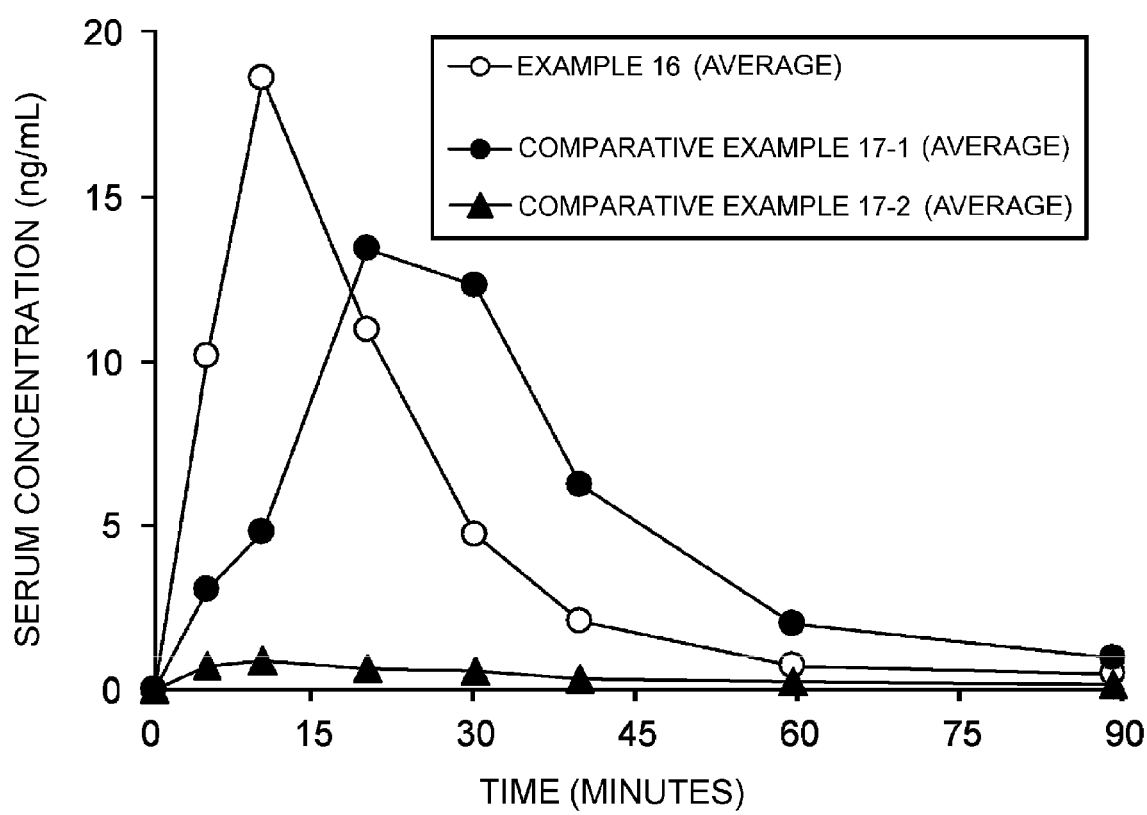

FIG. 13 is a graph showing the time course of serum PTH (1-34) concentration after administration of a nasal PTH(1-34) preparation to the monkeys.

Figure 14:
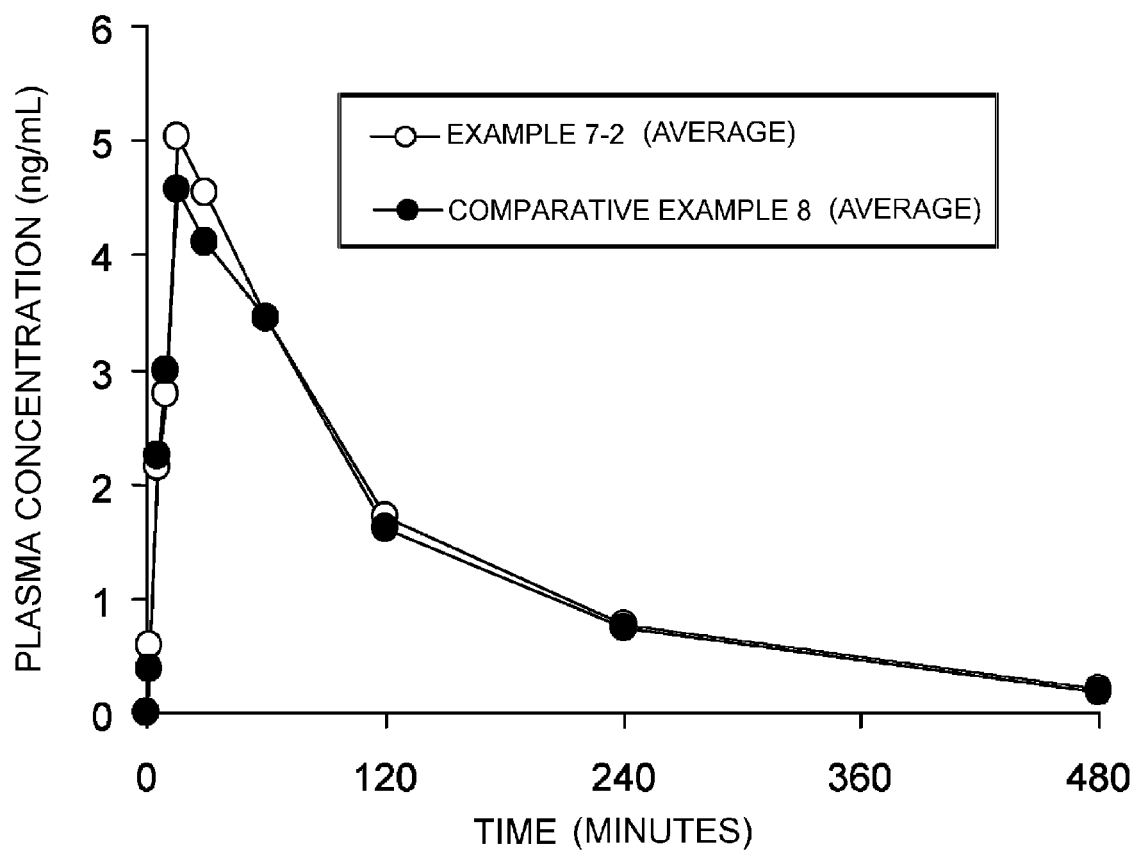

FIG. 14 is a graph showing the time course of plasma fentanyl concentration after administration of a nasal fentanyl preparation to the monkeys.

MODE FOR CARRYING OUT THE INVENTION

An embodiment of the nasal preparations of the present invention is nasal preparations comprising at least a complex of a physiologically active substance and a powder flowability-improving component comprising crystalline cellulose (A) (first crystalline cellulose) that has an untapped bulk density of 0.13 to 0.29 g/cm$^3$, a specific surface area of 1.3 m$^2$/g or more, an average particle diameter of 30 μm or less, and an angle of repose of 55° or more; tribasic calcium phosphate (B); and crystalline cellulose (C) (second crystalline cellulose) that has an untapped bulk density of 0.26 to 0.48 g/cm$^3$, a specific surface area of 1.3 m$^2$/g or less, an angle of repose of 50° or less, and an average particle diameter of 150 μm or less.

In general, "crystalline cellulose" that can be used in the present invention includes crystalline cellulose obtained by decomposing cellulose materials such as pulp by either or both of acid and alkaline hydrolyses, then purifying the hydrolysate, and crushing or grinding it before, during, or after drying.

More specifically, various types of Ceolus® and their derivatives can be used in the present invention after fine grinding using a high-speed rotary impact mill or air attrition mill as necessary, and size sorting for particles with a desired particle diameter; for example, crystalline cellulose whose average particle diameter is at most 30 μm and specific surface area is 1.3 m$^2$/g (Japanese Patent Application Kokoku Publication No. (JP-B) H05-038732 (examined, approved Japanese patent application published for opposition)), compositions comprising 35% to 80% microcrystalline cellulose aggregates and water (JP-B S39-12469), and crystalline cellulose whose average polymerization degree is 60 to 375, apparent specific volume is 1.60 to 3.10 cc/g, angle of repose is 35° to 42°, powder flowability is 200, and mesh fraction is 2 to 80 (W/W) % (JP-B S56-38128).

Herein, "first crystalline cellulose (A)" refers to the above-described crystalline cellulose that have an untapped bulk density of 0.13 to 0.29 g/cm$^3$, a specific surface area of 1.3 m$^2$/g or more, an average particle diameter of 30 μm or less, and an angle of repose of 55° or more.

The untapped bulk density of a first crystalline cellulose (A) is preferably 0.21 to 0.28 g/cm$^3$. The specific surface area is preferably 1.8 to 6.0 m$^2$/g, and more preferably 2.0 to 3.5 m$^2$/g. The average particle diameter is preferably 10 to 25 μm, and more preferably 12 to 22 μm. The angle of repose is preferably 55° to 75°, and more preferably 59° to 70°.

Specifically, such crystalline cellulose includes crystalline cellulose products that are available under the trade names of Ceolus® PH-F20JP and Avicel® PH-105 from Asahi Kasei Chemicals Corporation and FMC Corporation (US), respectively, and can be used as they are or after they are sorted. Ceolus® PH-F20JP is a crystalline cellulose disclosed in JP-A (Kokai) S63-267731, and reported to be able to drastically increase the binder effect in tablet formation.

"Tribasic calcium phosphate (B)" (also known as hydroxyapatite) used in the present invention is represented by the formula: $3Ca_3(PO_4)_2.Ca(OH)_2$, and is added to improve flowability. The tribasic calcium phosphate that can be used in the present invention is not particularly limited; however, in consideration of the dispersity in crystalline cellulose mixtures, its average particle diameter is preferably 100 μm or less, more preferably 10 to 75 μm, and even more preferably 10 to 50 μm.

The ratio of tribasic calcium phosphate added is not particularly limited, as long as it does not affect nasal drug absorption and can increase the flowability of preparations. However, the content of tribasic calcium phosphate (B) is 0.1 to 10 (W/W) %, preferably 0.5 to 5.0 (W/W) % of the total weight of the first crystalline cellulose (A), tribasic calcium phosphate (B), and second crystalline cellulose (C) ((A)+(B)+(C)).

The "second crystalline cellulose (C)" used in the present invention refers to crystalline cellulose with an untapped bulk density of 0.26 to 0.48 g/cm$^3$, a specific surface area of 1.3 m$^2$/g or less, an angle of repose of 50° or less, and an average particle diameter of 150 μm or less. The second crystalline cellulose is added to improve flowability.

The untapped bulk density of a second crystalline cellulose (C) is preferably 0.30 to 0.46 g/cm$^3$, more preferably 0.38 to 0.43 g/cm$^3$. The specific surface area is preferably 0.4 to 1.3 m$^2$/g, and more preferably 0.5 to 1.0 m$^2$/g. The average particle diameter is preferably 30 to 100 μm, and more preferably 40 to 75 μm. The angle of repose is preferably 30° to 50°, and more preferably 35° to 45°.

Specifically, such second crystalline cellulose includes crystalline cellulose products that are available under the trade names of Ceolus®, and Avicel® PH-101, PH-102, PH-301, and PH-302 from Asahi Kasei Chemicals Corporation and FMC Corporation (US); and can be used as they are or after they are sorted. Particularly preferred second crystalline cellulose includes crystalline cellulose products that are available under the trade names of Ceolus® PH-301 and Avicel® PH-301.

The ratio of second crystalline cellulose (C) added is not particularly limited, as long as it does not affect nasal drug absorption and can increase the flowability of preparations. However, the content is 5 to 30 (W/W) %, preferably 10 to 20 (W/W) % of the total weight of the first crystalline cellulose (A), tribasic calcium phosphate (B), and second crystalline cellulose (C) ((A)+(B)+(C)).

The flowability-improving component used in this embodiment comprises a first crystalline cellulose (A), tribasic calcium phosphate (B), and a second crystalline cellulose (C). Such flowability-improving components are preferably powder.

The angle of repose of the flowability-improving component in this embodiment depends on the ratios of added tribasic calcium phosphate and second crystalline cellulose. The angle is preferably 35° to 55°, and more preferably 40° to 53°. The flowability-improving component can drastically increase flowability compared to when only a first crystalline cellulose is used as a carrier.

Furthermore, the angles of repose of the nasal preparations in this embodiment depend on the repose angles of the above-described flowability-improving components, the type and ratio of the added physiologically active substance, and the like. The angle is preferably 35° to 55°, and more preferably 40° to 53°. The flowability of the nasal preparations can be increased drastically as compared to nasal preparations using only a first crystalline cellulose as the carrier.

Complexes comprising the above-described flowability-improving component and a physiologically active substance in this embodiment can be produced by mixing the above-described first crystalline cellulose (A), tribasic calcium phosphate (B), second crystalline cellulose (C), and physiologically active substance while applying a shearing force.

In preparations containing a complex produced as such, it is not necessary that all of the first crystalline cellulose (A), tribasic calcium phosphate (B), second crystalline cellulose (C), and physiologically active substance contained in the preparations form the complex. As long as at least one complex is formed in the preparations, they are included in the present invention.

Specifically, in this embodiment, the nasal preparations can be prepared using conventional methods that homogeneously mix powdery drugs with powdery flowability-improving components (for example, mortar, V-blender, and high shear mixer/stirrer). If required, malaxation after addition of water, freeze-drying, and a sorting step can be incorporated into the methods.

The order of mixing is not particularly limited. The mixing methods include methods that mix a physiologically active substance with a first crystalline cellulose, add a second crystalline cellulose, and finally add and mix tribasic calcium phosphate; methods that first mix a physiologically active substance, second crystalline cellulose, and tribasic calcium phosphate together, and then add a first crystalline cellulose; and methods that mix a physiologically active substance with a first crystalline cellulose, and then add a second crystalline cellulose and tribasic calcium phosphate simultaneously.

An alternative embodiment of the present invention is nasal preparations comprising at least a complex of a physiologically active substance and a powder flowability-improving component comprising crystalline cellulose (A) (first crystalline cellulose) with an untapped bulk density of 0.13 to 0.29 g/cm$^3$, a specific surface area of 1.3 m$^2$/g or more, an average particle diameter of 30 μm or less, and an angle of repose of 55° or more;

tribasic calcium phosphate (B); and starch (D) with an untapped bulk density of 0.35 to 0.65 g/cm$^3$, a specific surface area of 1.3 m$^2$/g or less, an angle of repose of 55° or less, and an average particle diameter of 150 μm or less.

The same first crystalline cellulose described above can be used as the first crystalline cellulose in this embodiment.

The same tribasic calcium phosphate described above can be used as the tribasic calcium phosphate in this embodiment.

The ratio of added tribasic calcium phosphate used in this embodiment is not particularly limited, as long as it does not affect nasal drug absorption and can increase the flowability of preparations. However, the ratio is 0.1 to 10 (W/W) %, preferably 0.5 to 5.0 (W/W) % of the total weight of the first crystalline cellulose (A), tribasic calcium phosphate (B), and starch (D) ((A)+(B)+(D)).

"Starch (D)" used in the present invention refers to particles with an untapped bulk density of 0.35 to 0.65 g/cm$^3$, a specific surface area of 1.3 m$^2$/g or less, an angle of repose of 55° or less, and an average particle diameter of 150 μm or less. Such starch is added to increase flowability.

The materials for starch of the present invention include corn and potato, but are not limited thereto.

The untapped bulk density of starch (D) is preferably 0.35 to 0.60 g/cm$^3$, and more preferably 0.40 to 0.60 g/cm$^3$. The specific surface area is preferably 0.5 to 1.3 m$^2$/g, and more preferably 0.7 to 1.0 m$^2$/g. The average particle diameter is preferably 30 to 100 μm, and more preferably 40 to 70 μm. The angle of repose is preferably 40° to 50°.

Specifically, such starch (D) includes cornstarch (Merck).

The ratio of added starch (D) is not particularly limited, as long as it does not affect nasal drug absorption and can increase the flowability of preparations. However, the ratio is preferably 5 to 30 (W/W) %, more preferably 10 to 20 (W/W) % of the total weight of the first crystalline cellulose (A), tribasic calcium phosphate (B), and starch (D) ((A)+(B)+(D)).

The flowability-improving component used in this embodiment comprises a first crystalline cellulose (A), tribasic calcium phosphate (B), and starch (D). Such flowability-improving components are preferably powder.

In this embodiment, the angle of repose of a flowability-improving component depends on the ratios of added tribasic calcium phosphate and starch. The angle is preferably 35° to 55°, and more preferably 40° to 53°. Thus, the flowability-improving component can drastically increase flowability compared to when only a first crystalline cellulose is used as the carrier.

The same physiologically active substances described above can be used as the physiologically active substance in this embodiment.

The angle of repose of the nasal preparations in this embodiment depends on the angle of repose of the above-described flowability-improving component, the type and ratio of the added physiologically active substance, and the like. The angle is preferably 35° to 55°, and more preferably 40° to 53°. The flowability of the nasal preparations can be drastically increased as compared to nasal preparations using only a first crystalline cellulose as the carrier.

Complexes comprising the above-described flowability-improving component and physiologically active substance can be produced by mixing the above-described first crystalline cellulose (A), tribasic calcium phosphate (B), starch (D), and the physiologically active substance while applying a shearing force.

In preparations containing the complex produced as described above, it is not necessary that all of the first crystalline cellulose (A), tribasic calcium phosphate (B), starch (D), and physiologically active substance contained in the preparations form complexes. As long as at least one complex is formed in the preparations, they are included in the present invention.

Specifically, the nasal preparations can be prepared using conventional methods that homogeneously mix powdery drugs with powdery carriers for nasal administration (for example, mortar, V-type mixer, and high-speed mixer/stirrer). If required, malaxation after addition of water, freeze-drying, and a sorting step can be incorporated into the methods.

The order of mixing is not particularly limited. The mixing methods include methods that mix a physiologically active substance with a first crystalline cellulose, add starch, and finally add and mix tribasic calcium phosphate; methods that first mix a physiologically active substance, starch, and tribasic calcium phosphate together, and then add a first crystalline cellulose; and methods that mix a physiologically active substance with a first crystalline cellulose, and then add starch and tribasic calcium phosphate simultaneously.

Specific powder properties of various kinds of crystalline cellulose (Ceolus®, Asahi Kasei Chemicals Corporation; Avicel®, FMC Corporation) and a starch product (Merck) are listed in Table 1.

determined using a laser-diffraction particle size distribution analyzer, and the "average particle diameters" of other crystalline cellulose products were determined based on the particle size distribution by a sorting method.

The "median diameter" refers to a diameter that divides particles into two groups of equal numbers: a group with greater diameters and a group with smaller diameters. The median diameter determined using a laser-diffraction particle size distribution analyzer corresponds to 50% volume in a determined cumulative particle size distribution curve.

The average particle diameter determined by a sorting method corresponds to 50 (W/W) % on a cumulative particle size distribution curve obtained by sorting 10 g of crystalline cellulose or starch of use for ten minutes on a electromagnetic sieve shaker, using standard sieves (which meet Japanese Industrial Standards (JIS)) layered in the order of aperture sizes 38 45, 53, 75, 106, 180, and 300 μm, and weighing the sample that remained on each sieve. This procedure is based on the second method of particle size distribution test, among the general tests described in the Japanese Pharmacopoeia, Fourteenth Edition, Part I.

Herein, "untapped bulk density" can be measured based on the second method for determination of bulk and tapped densities, among the general tests described in Part I of Supplement I to Japanese Pharmacopoeia, Fourteenth Edition. Specifically, the density can be determined by pouring the sample evenly from above into a cylindrical vessel with an inner diameter of 46 mm and a height of 110 mm (measured volume, 180 ml) through a 1000-μm JIS standard sieve, and weighing the sample after smoothly leveling off the top of the vessel.

The untapped bulk density varies depending on particle size, shape, cohesion force, and such. In general, the untapped bulk density tends to decrease as the particle takes on a more irregular shape away from the sphere shape. Furthermore, as the particle diameter becomes smaller, the force of interparticle cohesion, rather than the weight of particle itself, has more impact on the density, and thus the untapped bulk den-

TABLE 1

Powder properties

| | | CRYSTALLINE CELLULOSE | | | | | | |
|---|---|---|---|---|---|---|---|---|
| | | FIRST CRYSTALLINE CELLULOSE | | SECOND CRYSTALLINE CELLULOSE | | | | STARCH |
| ITEM | | PH-F20JP | PH-105 | PH-101 | PH-102 | PH-301 | PH-302 | STARCH |
| MEAN PARTICLE DIAMETER[1] | (μm) | 20 | 20 | 50 | 90 | 50 | 90 | — |
| ACTUAL MEAN PARTICLE DIAMETER | (μm) | 19 | 18 | 55 | 95 | 55 | 100 | 68 |
| UNTAPPED BULK DENSITY[1] | (g/cm$^3$) | 0.23 | 0.25 | 0.29 | 0.30 | 0.41 | 0.43 | — |
| ACTUAL UNTAPPED BULK DENSITY | (g/cm$^3$) | 0.24 | 0.27 | 0.32 | 0.33 | 0.42 | 0.44 | 0.41 |
| ACTUAL SPECIFIC SURFACE AREA | (m$^2$/g) | 2.23 | 2.27 | 1.28 | 1.30 | 0.87 | 0.92 | 0.92 |
| REPOSE ANGLE[1] | (DEGREE) | >60 | — | 45 | 42 | 41 | 38 | — |
| ACTUAL REPOSE ANGLE | (DEGREE) | 62 | 59 | 46 | 42 | 42 | 38 | 47 |

[1]Catalog values (Ceolus, Avicel,
PH-F20JP, Ceolus ® PH-F20JP;
PH-105, Avicel ® PH-105;
PH-101, Ceolus ® PH-101;
PH-102, Ceolus ® PH-102;
PH-301, Ceolus ® PH-301;
PH-302, Ceolus ® PH-302;
STARCH, cornstarch.

Herein, the "average particle diameters" of Ceolus® PH-F20JP and Avicel® PH-105 were median diameters sity tends to be smaller. However, there was no significant difference in the untapped bulk density between Ceolus®

PH-101 and PH-102, or Ceolus® PH-301 and PH-302, which belong to the same series but differ in their average particle diameters. Therefore, in crystalline cellulose, the untapped bulk density is assumed to vary depending on factors other than particle diameter, for example, the difference in particle morphology such as particle shape. The untapped bulk density is an important parameter that characterizes particles.

The measured untapped bulk densities were compared to the values shown in catalogs to assess the adequacy of the method for determining bulk densities employed in this examination. The measured densities were not different from the values shown in the catalogs.

Herein, the "specific surface area" can be determined by the second method for determination of specific surface area (BET method), among the general tests described in the Japanese Pharmacopoeia, Fourteenth Edition, Part I. Specifically, the specific surface area can be determined based on the BET formula from the amount of nitrogen molecules adsorbed onto the powder surface after six hours of pre-vacuation at a fixed temperature (77.35 Kelvin).

The specific surface area varies depending on particle size, surface properties, presence of pores, and the like. In general, as the particle diameter becomes smaller, the specific surface area tends to be greater. However, there was no significant difference in the specific surface area between Ceolus® PH-101 and PH-102 or Ceolus® PH-301 and PH-302, which belong to the same series but differ in their average particle diameters. As inferred from JP-B S56-38128, the reason is because crystalline cellulose is originally present as porous powder, and the specific surface area is not significantly altered even when the diameter is changed as a result of sorting. Specifically, the specific surface area of crystalline cellulose is assumed to vary depending on factors other than particle diameter, for example, particle morphology such as particle surface structure and number of pores. The great specific surface areas observed in Ceolus® PH-F20JP and Avicel® PH-105 become important values that indicate particle characteristics for crystalline cellulose with characteristic particle morphology.

Herein, the "angle of repose" refers to a slope angle that can maintain a pile of powder accumulated in a way that it does not spontaneously collapse when dropped in the gravitational field. The angle can be measured by a funnel flow method. For example, measurement by the funnel flow method calculates the slope for a pile of powder that has been freely dropped through a funnel onto a disc and piled on a horizontal plane, based on the diameter of the circular bottom plane and the height of the powder pile.

The angle of repose varies depending on particle size, surface properties, and the like. In general, the angle tends to be greater as the particle diameter becomes smaller. The angle of repose serves as an indicator for powder flowability, and a smaller angle of repose means higher powder flowability.

The measured angles of repose were compared with the catalog values to assess the adequacy of the conventional funnel flow method for determining the angles of repose employed in this examination. There was no difference between the measured angles and catalog values.

The average particle diameter, untapped bulk density, specific surface area, and angle of repose are representative characteristic values for identifying the physical properties of crystalline cellulose. The characteristic values of untapped bulk density, specific surface area, and angle of repose are complex parameters that are not simply dependent on the particle diameter alone. Crystalline cellulose can be characterized by specifying the respective particle properties. Those skilled in the art can readily determine the respective parameters according to the above-described measurement methods.

In another embodiment of the present invention, other carriers or bases, pH adjustors, preservatives, stabilizers, flavors, and absorbefacients can be added to the above-described nasal preparations, as long as there is no adverse effect on the objective of the present invention. The carriers or bases include, for example, hydroxypropyl cellulose, alginic acid, chitosan, and gamma polyglutamate. The pH adjustors include, for example, dibasic sodium phosphate, citric acid, and sodium citrate. The preservatives include, for example, benzalkonium chloride. The flavors include, for example, D-sorbitol, glycyrrhizia, saccharin, and stevia. The absorbefacients include, for example, bile acid.

Furthermore, when the divalent calcium ion of added tribasic calcium phosphate enhances multimer formation of negatively charged drugs via coordinate bonds or the like, and as a result reduces the nasal absorption of drugs, sodium alginate, sodium citrate, sodium glutamate, EDTA, or such can be added as a substance to capture divalent calcium ions.

All prior art documents cited herein are incorporated herein by reference.

EXAMPLES

Hereinbelow, the present invention will be described more specifically with reference to the Examples, but is not to be construed as being limited thereto.

The angle of repose serves as a representative indicator for assessing powder flowability. In general, larger angle means poorer powder flowability. Table 2 shows the angles of repose determined when various ratios ((W/W) % of the total weight) of magnesium stearate (Wako Pure Chemical Industries), talc (Wako Pure Chemical Industries), tribasic calcium phosphate (Taihei Chemical Industrial Co., particles selected to have a diameter of 38 μm or less by sorting), Ceolus® PH-301 (Asahi Kasei Chemicals Corporation), or cornstarch (Merck) was added to Ceolus® PH-F20JP (Asahi Kasei Chemicals Corporation), a crystalline cellulose product (first crystalline cellulose) serving as an effective carrier for nasal administration.

The above-described components were prepared by homogeneously mixing Ceolus® PH-F20JP with one selected from magnesium stearate, talc, tribasic calcium phosphate, Ceolus® PH-301, and cornstarch in a mortar under conditions of room temperature and a relative humidity of 60% or less.

TABLE 2

Angles of repose measured when a single agent was added

| ADDITION RATIO ((W/W) %) | St-Mg | TALC | TCP | PH-301 | STARCH |
|---|---|---|---|---|---|
| 0.5% | 60.0 | 57.1 | 56.2 | — | — |
| 1.0% | 57.1 | 57.1 | 55.2 | — | — |
| 2.0% | 56.2 | 56.2 | 54.2 | — | — |
| 5.0% | 55.7 | 55.7 | 53.1 | 59.6 | 57.1 |
| 10.0% | 56.2 | 55.2 | 50.8 | 58.4 | 57.1 |
| 20.0% | — | — | — | 56.7 | 57.1 |

St-Mg, magnesium stearate;
TALC, talc;
TCP, tribasic calcium phosphate;
PH-301, Ceolus ® PH-301;
STARCH, cornstarch.

In comparison with when only Ceolus® PH-F20JP was added (62°), the angle of repose was slightly improved by adding magnesium stearate or talc. However, neither magnesium stearate nor talc produced a sufficient flowability-improving effect. On the other hand, the addition of tribasic calcium phosphate reduced the angle of repose according to the ratio of addition, and its effect was stronger than that of magnesium stearate or talc. Alternatively, when Ceolus® PH-301 or cornstarch was added at a ratio of 5% to 20%, the effect of reducing the angle of repose was barely observed even when compared with the addition of magnesium stearate or talc.

Table 3, FIGS. 1-1 and 1-2 show the angles of repose determined when one or two agents selected from one of magnesium stearate (Wako Pure Chemical Industries), talc (Wako Pure Chemical Industries), and tribasic calcium phosphate (Taihei Chemical Industrial Co., particles selected to have a diameter of 38 μm or less by sorting), and one of Ceolus® PH-101 (Asahi Kasei Chemicals Corporation), Ceolus® PH-102 (Asahi Kasei Chemicals Corporation), Ceolus® PH-301 (Asahi Kasei Chemicals Corporation), Ceolus® PH-302 (Asahi Kasei Chemicals Corporation), and cornstarch (Merck) as the second crystalline cellulose, were added at various ratios ((W/W) % of the total weight) to Ceolus® PH-F20JP (Asahi Kasei Chemicals Corporation), which is a crystalline cellulose product (the first crystalline cellulose) serving as an effective carrier for nasal administration.

The above-described components were prepared by the following procedure. First, Ceolus® PH-F20JP was mixed with any one selected from Ceolus® PH-101, Ceolus® PH-102, Ceolus® PH-301, Ceolus® PH-302, and cornstarch in a mortar under the conditions of room temperature and a relative humidity of 60% or less. Then, any one selected from magnesium stearate, talc, and tribasic calcium phosphate was added, and the resulting mixture was mixed homogeneously.

of tribasic calcium phosphate as a fluidizing agent and crystalline cellulose or cornstarch as a flowability-enhancing agent was found to produce the flowability-improving effect when compared with the use of it alone.

In particular, when crystalline cellulose was used as a flowability-enhancing agent in combination, Ceolus® PH-301 was revealed to be most effective. Flowability was improved even when only 5 (W/W) % of Ceolus® PH-301 was added.

Alternatively, the combined use of cornstarch as a flowability-enhancing agent at a content of 5 (W/W) % or more was also revealed to improve flowability.

Furthermore, when tribasic calcium phosphate was used in combination with a crystalline cellulose product other than Ceolus® PH-301, the combination effect was detected when crystalline cellulose was added as a flowability-enhancing agent at a ratio of 20% or more (FIG. 2).

It is noteworthy that crystalline cellulose and starch had almost no contribution on the flowability-improving effect when used alone, but enhanced flowability when used in combination with tribasic calcium phosphate.

Figures 1, 3:
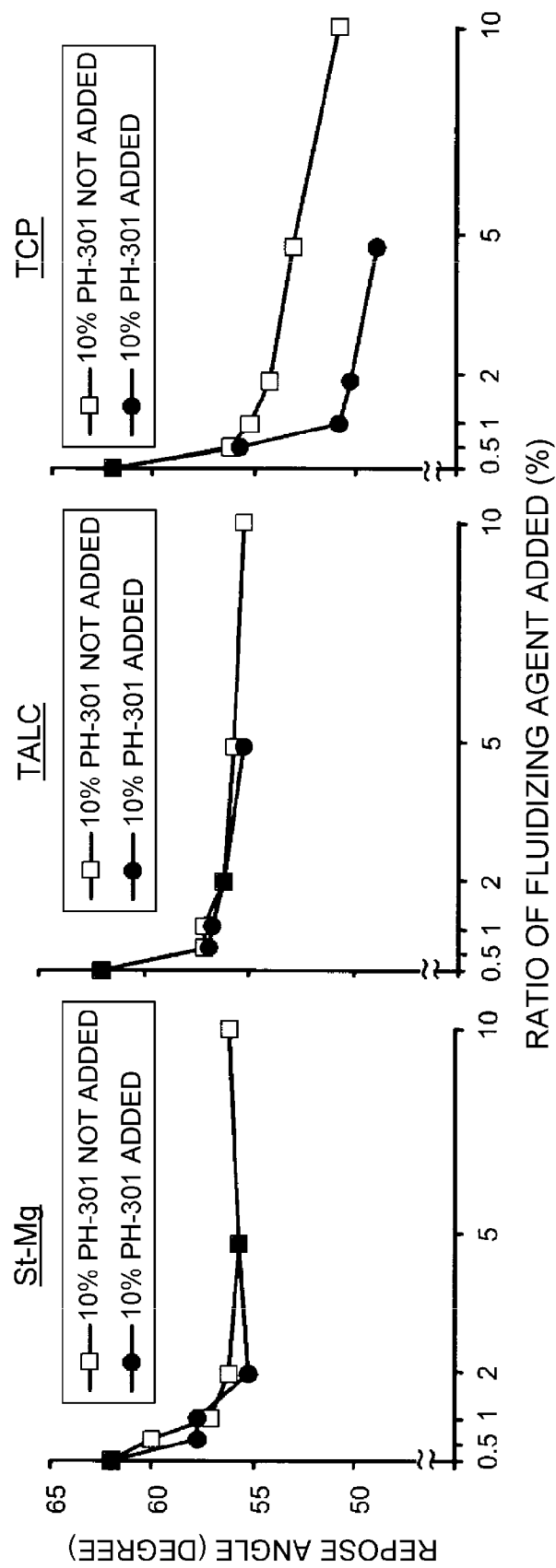
Figures 2, 3:
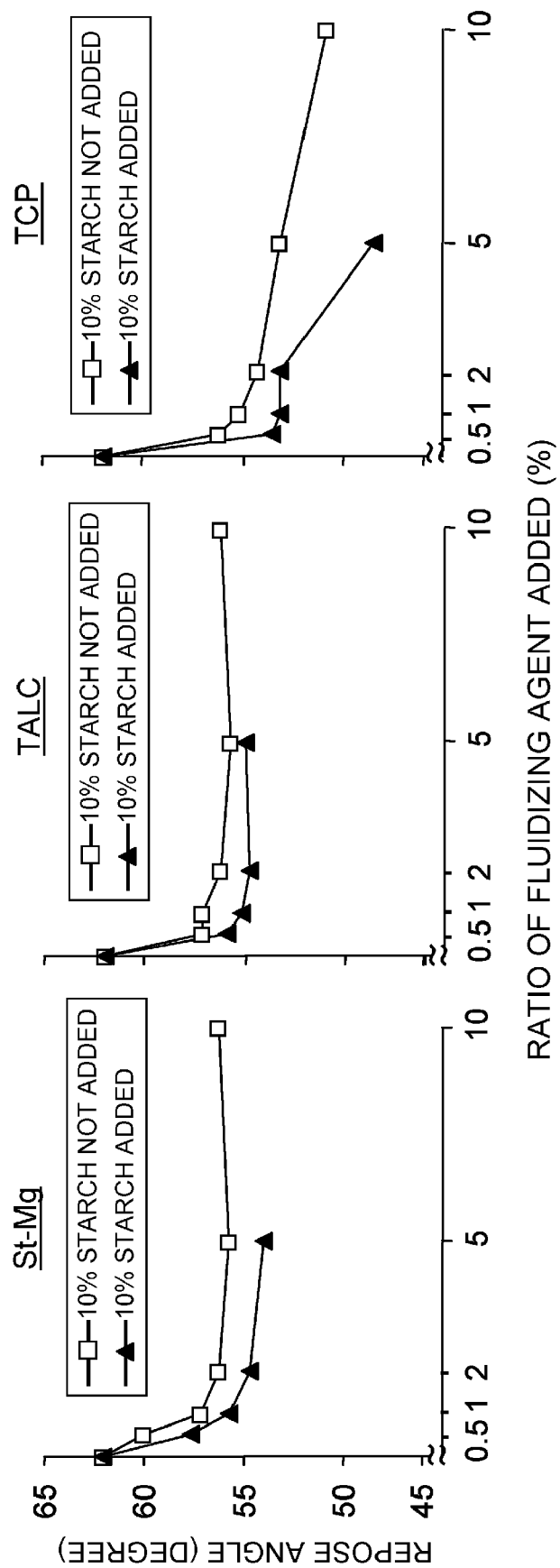

Furthermore, as shown in FIG. 3-1, the flowability-improving effect of the combined use of tribasic calcium phosphate and Ceolus® PH-301 was enhanced according to the ratio of tribasic calcium phosphate added, demonstrating that flowability can be controlled by adjusting the ratio of tribasic calcium phosphate.

In addition, as shown in FIG. 3-2, it was demonstrated that the flowability-improving effect of the combined use of tribasic calcium phosphate and cornstarch could be markedly improved by adding 5 (W/W) % or more of tribasic calcium phosphate.

TABLE 3

Angles of repose measured when a fluidizing agent and a flowability-enhancing agent were used in combination

| ADDITION RATIO | | 0.5% | | | 1.0% | | | 2.0% | | | 5.0% | | |
|---|---|---|---|---|---|---|---|---|---|---|---|---|---|
| ((W/W) %) | | St-Mg | TALC | TCP | St-Mg | TALC | TCP | St-Mg | TALC | TCP | St-Mg | TALC | TCP |
| 5% | PH-101 | — | — | — | — | — | 55.2 | — | — | 54.7 | — | — | — |
|  | PH-102 | — | — | — | — | — | 55.2 | — | — | 55.2 | — | — | — |
|  | PH-301 | — | — | 54.2 | 55.7 | 56.2 | 51.4 | 55.7 | 54.7 | 51.4 | — | — | 49.6 |
|  | PH-302 | — | — | — | — | — | 54.2 | — | — | 54.2 | — | — | — |
|  | STARCH | — | — | 53.7 | — | — | 53.1 | — | — | 54.2 | — | — | 50.8 |
| 10% | PH-101 | — | — | — | 58.4 | 56.7 | 54.7 | 56.7 | 56.2 | 56.7 | — | — | — |
|  | PH-102 | — | — | — | 58.4 | 55.7 | 55.2 | 56.2 | 55.2 | 55.2 | — | — | — |
|  | PH-301 | 57.7 | 56.9 | 54.7 | 57.7 | 56.7 | 50.8 | 55.2 | 56.2 | 50.2 | 55.7 | 55.2 | 48.9 |
|  | PH-302 | — | — | — | 56.7 | 55.7 | 54.2 | 56.2 | 56.2 | 54.2 | — | — | — |
|  | STARCH | 57.7 | 55.9 | 53.5 | 55.7 | 55.2 | 53.1 | 54.7 | 54.7 | 53.1 | 54.0 | 54.9 | 48.5 |
| 20% | PH-101 | — | — | — | — | — | 53.7 | — | — | 53.7 | — | — | — |
|  | PH-102 | — | — | — | — | — | 52.6 | — | — | 52.6 | — | — | — |
|  | PH-301 | — | — | 53.1 | 56.2 | 54.7 | 48.2 | 53.7 | 54.2 | 48.2 | — | — | 47.6 |
|  | PH-302 | — | — | — | — | — | 51.4 | — | — | 52.6 | — | — | — |
|  | STARCH | — | — | 55.1 | — | — | 51.4 | — | — | 52.6 | — | — | 48.5 |

St-Mg, magnesium stearate;
TALC, talc;
TCP, tribasic calcium phosphate;
PH-101, Ceolus ® PH-101;
PH-102, Ceolus ® PH-102;
PH-301, Ceolus ® PH-301;
PH-302, Ceolus ® PH-302;
STARCH, cornstarch.

There was no difference in the angle of repose between using magnesium stearate or talc as a fluidizing agent in combination with crystalline cellulose or cornstarch as a flowability-enhancing agent, and using magnesium stearate or talc alone. The combination was not found to produce any flowability-enhancing effect. By contrast, the combined use Next, further investigation was carried out by adding various drugs to combinations of the flowability-improving components observed to have the flowability-improving effect. The combinations contain Ceolus® PH-F20JP (Asahi Kasei Chemicals Corporation) as a carrier for nasal administration, either Ceolus® PH-301 (Asahi Kasei Chemicals Corporation) or cornstarch (Merck) as a flowability-enhancing agent, and tribasic calcium phosphate (Taihei Chemical Industrial Co., particles selected to have a diameter of 38 μm or less by sorting) as a fluidizing agent.

According to the formulations listed in Table 4, various preparations were prepared under the conditions of room temperature and a relative humidity of 60% or less. When the flowability-improving component comprised a first crystalline cellulose and tribasic calcium phosphate, preparations were prepared by first mixing a physiologically active substance and Ceolus® PH-F20JP together, and then mixing tribasic calcium phosphate with the resulting mixture.

Alternatively, when the flowability-improving component comprised a first crystalline cellulose, tribasic calcium phosphate, and a second crystalline cellulose or starch, preparations were prepared by first mixing a physiologically active substance and Ceolus® PH-F20JP together, then adding Ceolus® PH-301 or cornstarch, and finally adding tribasic calcium phosphate to the resulting mixture in a mortar.

The drugs that are used are granisetron hydrochloride (Chemagis), ondansetron hydrochloride (LKT Laboratories), and tropisetron hydrochloride (LKT Laboratories), all of which are antiemetic agents; morphine hydrochloride trihydrate (Takeda Pharmaceutical Company), fentanyl citrate (Fine Chemicals), and oxycodone hydrochloride (Mallinckrodt), all of which are analgesic agents; sumatriptan succinate (Tronto Research Chemicals) and zolmitriptan (Lundbeck), both of which are antimigraine agents; beclomethasone dipropionate (USP Convention) and ketotifen maleate (LKT Laboratories), both of which are therapeutic agents for rhinitis; human insulin (Intergen), a therapeutic agent for diabetes; human menopausal gonadotropin (Wako Pure Chemical Industries), a therapeutic agent for infertility; and parathyroid hormone (1-34) (Bachem), a therapeutic agent for osteoporosis.

TABLE 4

List of formulations for nasal preparations containing various drugs

| | | | CARRIER FOR NASAL ADMINISTRATION | FLOWABILITY-ENHANCING AGENT | | LUBRICANT/FLUIDIZING AGENT | | | TOTAL |
|---|---|---|---|---|---|---|---|---|---|
| EXAMPLE | | DRUG* | PH-F20JP | PH-301 | STARCH | St-Mg | TALC | TCP | AMOUNT |
| GRANI-SETRON | EXAMPLE 1 | 0.40 g | 8.45 g | 1 g | — | — | — | 0.1 g | 10 g |
| | EXAMPLE 2 | 0.40 g | 7.45 g | 2 g | — | — | — | 0.1 g | 10 g |
| ONDAN-SETRON | EXAMPLE 3-1 | 0.40 g | 8.40 g | 1 g | — | — | — | 0.1 g | 10 g |
| | EXAMPLE 3-2 | 3.20 g | 4.86 g | 1 g | — | — | — | 0.15 g | 10 g |
| MORPHINE | EXAMPLE 4 | 0.80 g | 7.85 g | 1 g | — | — | — | 0.1 g | 10 g |
| | EXAMPLE 5-1 | 0.80 g | 7.75 g | 1 g | — | — | — | 0.2 g | 10 g |
| | EXAMPLE 5-2 | 4.50 g | 2.97 g | 1 g | — | — | — | 0.1 g | 10 g |
| | EXAMPLE 6 | 0.80 g | 7.85 g | — | 1 g | — | — | 0.1 g | 10 g |
| FENTANYL | EXAMPLE 7-1 | 0.06 g | 8.81 g | 1 g | — | — | — | 0.1 g | 10 g |
| | EXAMPLE 7-2 | 0.04 g | 8.86 g | 1 g | — | — | — | 0.08 g | 10 g |
| OXYCODONE | EXAMPLE 8 | 1.50 g | 7.23 g | 1 g | — | — | — | 0.1 g | 10 g |
| SUMA-TRIPTAN | EXAMPLE 9-1 | 1.20 g | 7.22 g | 1 g | — | — | — | 0.1 g | 10 g |
| | EXAMPLE 9-2 | 4.00 g | 3.30 g | 1 g | — | — | — | 0.1 g | 10 g |
| BECLO-METASONE | EXAMPLE 10 | 2.0 mg | 8.898 g | 1 g | — | — | — | 0.1 g | 10 g |
| KETOTIFEN | EXAMPLE 11 | 2.0 mg | 8.897 g | 1 g | — | — | — | 0.1 g | 10 g |
| INSULIN | EXAMPLE 12 | 121.7 mg (3200 U) | 8.78 g | 1 g | — | — | — | 0.1 g | 10 g |
| | EXAMPLE 13 | 121.7 mg (3200 U) | 8.68 g | 1 g | — | — | — | 0.2 g | 10 g |
| | EXAMPLE 14 | 121.7 mg (3200 U) | 8.78 g | — | 1 g | — | — | 0.1 g | 10 g |
| HMG | EXAMPLE 15 | 9.6 mg (500 U) | 0.435 g | 0.05 g | — | — | — | 0.005 g | 0.5 g |
| PTH(1-34) | EXAMPLE 16 | 1.6 mg** | 0.430 g | 0.05 g | — | — | — | 0.004 g | 0.5 g |
| ZOLMI-TRIPTAN | EXAMPLE 17 | 1.00 g | 7.90 g | 1 g | — | — | — | 0.1 g | 10 g |

PH-F20JP, Ceolus ® PH-F20JP;
PH-301, Ceolus ® PH-301;
STARCH, cornstarch;
St-Mg, magnesium stearate;
TALC, talc;
TCP, tribasic calcium phosphate.
HMG, human menopausal gonadotrophin;
PTH(1-34), parathyroid hormone.
*Free base equivalent.
**Peptide content 76%.

Meanwhile, as comparative examples, some nasal preparations were prepared and assessed. The preparations were prepared by mixing various drugs with Ceolus® PH-F20JP (Asahi Kasei Chemicals Corporation) as a carrier for nasal administration in a mortar, or by mixing various drugs with Ceolus® PH-F20JP (Asahi Kasei Chemicals Corporation) as a carrier for nasal administration, either Ceolus® PH-301 (Asahi Kasei Chemicals Corporation) or cornstarch (Merck) as a flowability-enhancing agent, and either magnesium stearate (Wako Pure Chemical Industries) or talc (Wako Pure Chemical Industries) as a lubricant/fluidizing agent.

According to the formulations listed in Table 5, various preparations were prepared under the conditions of room temperature and a relative humidity of 60% or less by the procedure described below.

When only the first crystalline cellulose was used as a flowability-improving component, nasal preparations were prepared by mixing Ceolus® PH-F20JP with a physiologically active substance.

When the flowability-improving component included the first crystalline cellulose and a lubricant/fluidizing agent, nasal preparations were prepared by first mixing Ceolus® PH-F20JP with a physiologically active substance and then adding magnesium stearate or talc thereto.

When the flowability-improving component contained the first crystalline cellulose, a lubricant/fluidizing agent, and second crystalline cellulose or starch, nasal preparations were prepared by first mixing Ceolus® PH-F20JP with a physiologically active substance, then adding Ceolus® PH-301 or cornstarch, and finally adding magnesium stearate or talc thereto in a mortar.

TABLE 5

List of formulations for nasal preparations containing various drugs (Comparative Examples)

| | COMPARATIVE EXAMPLE | DRUG* | CARRIER FOR NASAL ADMINISTRATION PH-F20JP | FLOWABILITY-ENHANCING AGENT PH-301 | FLOWABILITY-ENHANCING AGENT STARCH | LUBRICANT/FLUIDIZING AGENT St-Mg | LUBRICANT/FLUIDIZING AGENT TALC | LUBRICANT/FLUIDIZING AGENT TCP | TOTAL AMOUNT |
|---|---|---|---|---|---|---|---|---|---|
| GRANISETRON | COMPARATIVE EXAMPLE 1 | 0.40 g | 9.55 g | — | — | — | — | — | 10 g |
| | COMPARATIVE EXAMPLE 2 | 0.40 g | 8.45 g | 1 g | — | 0.1 g | — | — | 10 g |
| ONDANSETRON | COMPARATIVE EXAMPLE 3 | 0.40 g | 9.5 g | — | — | — | — | — | 10 g |
| MORPHINE | COMPARATIVE EXAMPLE 4 | 0.80 g | 8.95 g | — | — | — | — | — | 10 g |
| | COMPARATIVE EXAMPLE 5 | 0.80 g | 7.85 g | 1 g | — | 0.1 g | — | — | 10 g |
| | COMPARATIVE EXAMPLE 6 | 0.80 g | 7.85 g | 1 g | — | — | 0.1 g | — | 10 g |
| | COMPARATIVE EXAMPLE 7 | 0.80 g | 7.85 g | — | 1 g | 0.1 g | — | — | 10 g |
| FENTANYL | COMPARATIVE EXAMPLE 8 | 0.06 g | 9.91 g | — | — | — | — | — | 10 g |
| OXYCODONE | COMPARATIVE EXAMPLE 9 | 1.50 g | 8.33 g | — | — | — | — | — | 10 g |
| SUMATRIPTAN | COMPARATIVE EXAMPLE 10-1 | 1.20 g | 8.32 g | — | — | — | — | — | 10 g |
| | COMPARATIVE EXAMPLE 10-2 | 1.20 g | 7.22 g | 1 g | — | 0.1 g | — | — | 10 g |
| BECLOMETASONE | COMPARATIVE EXAMPLE 11 | 2.0 mg | 9.998 g | — | — | — | — | — | 10 g |
| KETOTIFEN | COMPARATIVE EXAMPLE 12 | 2.0 mg | 9.997 g | — | — | — | — | — | 10 g |
| INSULIN | COMPARATIVE EXAMPLE 13 | 121.7 mg (3200 U) | 9.88 g | — | — | — | — | — | 10 g |
| | COMPARATIVE EXAMPLE 14 | 121.7 mg (3200 U) | 8.78 g | 1 g | — | 0.1 g | — | — | 10 g |
| | COMPARATIVE EXAMPLE 15 | 121.7 mg (3200 U) | 8.78 g | — | 1 g | — | 0.1 g | — | 10 g |
| HMG | COMPARATIVE EXAMPLE 16 | 9.6 mg (500 U) | 0.490 g | — | — | — | — | — | 0.5 g |
| PTH(1-34) | COMPARATIVE EXAMPLE 17-1 | 1.6 mg** | 0.498 g | — | — | — | — | — | 0.5 g |
| | COMPARATIVE EXAMPLE 17-2 | 1.6 mg** | 0.444 g | 0.05 g | — | 0.005 g | — | — | 0.5 g |
| ZOLMITRIPTAN | COMPARATIVE EXAMPLE 18 | 1.00 g | 9.00 g | — | — | — | — | — | 10 g |

PH-F20JP, Ceolus ® PH-F20JP;
PH-301, Ceolus ® PH-301;
STARCH, cornstarch;
St-Mg, magnesium stearate;
TALC, talc;
TCP, tribasic calcium phosphate.
HMG, human menopausal gonadotrophin;
PTH(1-34), parathyroid hormone.
*Free base equivalent.
**Peptide content 76%.

Table 6 shows the measurement results for the angles of repose of nasal preparations prepared according to the formulations shown in Tables 4 and 5.

TABLE 6

Angles of repose for various nasal preparations

|  | DRUG | REPOSE ANGLE (DEGREE) |
|---|---|---|
| GRANISETRON | EXAMPLE 1 | 51.8 |
|  | EXAMPLE 2 | 50.0 |
|  | COMPARATIVE EXAMPLE 1 | 57.0 |
|  | COMPARATIVE EXAMPLE 2 | 57.6 |
| ONDANSETRON | EXAMPLE 3-1 | 51.8 |
|  | EXAMPLE 3-2 | 52.0 |
|  | COMPARATIVE EXAMPLE 3 | 57.0 |
| MORPHINE | EXAMPLE 4 | 52.6 |
|  | EXAMPLE 5-1 | 50.1 |
|  | EXAMPLE 5-2 | 49.8 |
|  | EXAMPLE 6 | 52.6 |
|  | COMPARATIVE EXAMPLE 4 | 62.1 |
|  | COMPARATIVE EXAMPLE 5 | 58.8 |
|  | COMPARATIVE EXAMPLE 6 | 58.2 |
|  | COMPARATIVE EXAMPLE 7 | 58.2 |
| FENTANYL | EXAMPLE 7-1 | 51.8 |
|  | EXAMPLE 7-2 | 51.8 |
|  | COMPARATIVE EXAMPLE 8 | 61.6 |
| OXYCODONE | EXAMPLE 8 | 52.6 |
|  | COMPARATIVE EXAMPLE 9 | 62.1 |
| SUMATRIPTAN | EXAMPLE 9-1 | 51.8 |
|  | EXAMPLE 9-2 | 51.3 |
|  | COMPARATIVE EXAMPLE 10-1 | 61.6 |
|  | COMPARATIVE EXAMPLE 10-2 | 57.7 |
| BECLOMETASONE | EXAMPLE 10 | 50.8 |
|  | COMPARATIVE EXAMPLE 11 | 61.6 |
| KETOTIFEN | EXAMPLE 11 | 51.8 |
|  | COMPARATIVE EXAMPLE 12 | 62.1 |
| INSULIN | EXAMPLE 12 | 51.8 |
|  | EXAMPLE 13 | 50.1 |
|  | EXAMPLE 14 | 52.6 |
|  | COMPARATIVE EXAMPLE 13 | 59.4 |
|  | COMPARATIVE EXAMPLE 14 | 57.6 |
|  | COMPARATIVE EXAMPLE 15 | 56.3 |
| ZOLMITRIPTAN | EXAMPLE 17 | 50.1 |
|  | COMPARATIVE EXAMPLE 18 | 59.4 |

Regardless of the type of drug added, the nasal preparations of the present invention were shown to have an effect of reducing the angle of repose, that is, the flowability-improving effect. The same tendency in Table 3 was confirmed.

Next, carriers containing various flowability-improving components were tested for variation in the filling amount per capsule to assess the flowability-improving effect.

When a powder with poor flowability is used to fill capsules, in general, the filling amount tends to vary among capsules. This is because gaps tend to form among powder particles, and powder flow tends to be uneven due to poor flowability in pouring the powder into capsules. The variation in the filling amount per capsule markedly changes the amount of drug added, and results in variations in the single dosage of drug among capsules. Consequently, the uniformity in the filling amount per capsule contributes to the productivity of capsule preparations, and is an important factor for determining an adequate dosage.

Figure 4:
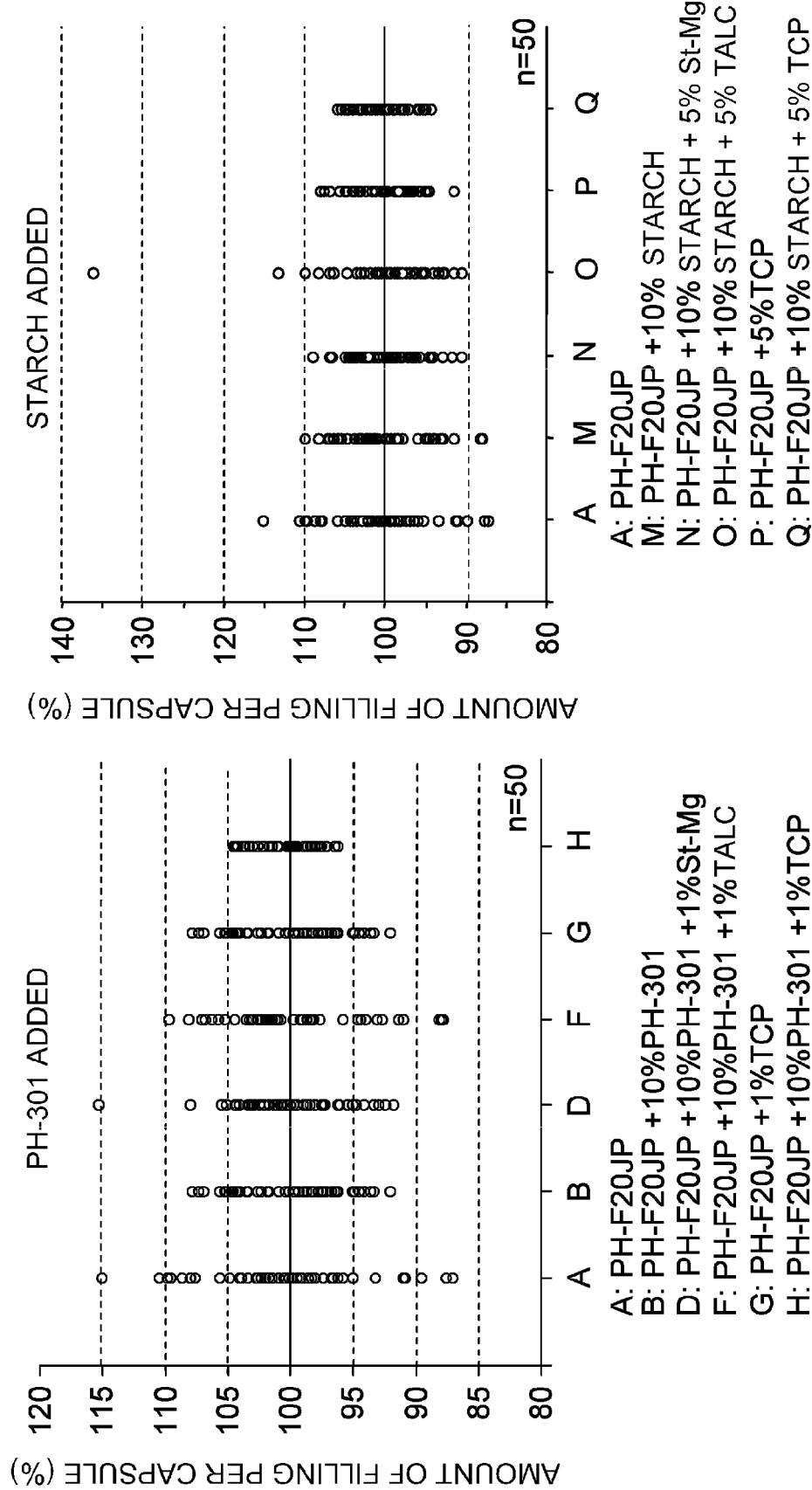
FIG. 4 shows variations in the filling amount when 50 capsules (gelatin, size 1) were filled with various compounding agents. The filling amount in each capsule is shown in percentage when the average filling amount is taken as standard. The various compounding agents used in the assessment include: fluidizing agents added alone to Ceolus® PH-F20JP, and fluidizing agents and flowability-enhancing agents added simultaneously to Ceolus® PH-F20JP. In these diagrams, "St-Mg" indicates magnesium stearate; "TALC" indicates talc; "TCP" indicates tribasic calcium phosphate; "PH-F20JP" indicates Ceolus® PH-F20JP; "PH-301" indicates Ceolus® PH-301; and "STARCH" indicates cornstarch.
Figure 5:
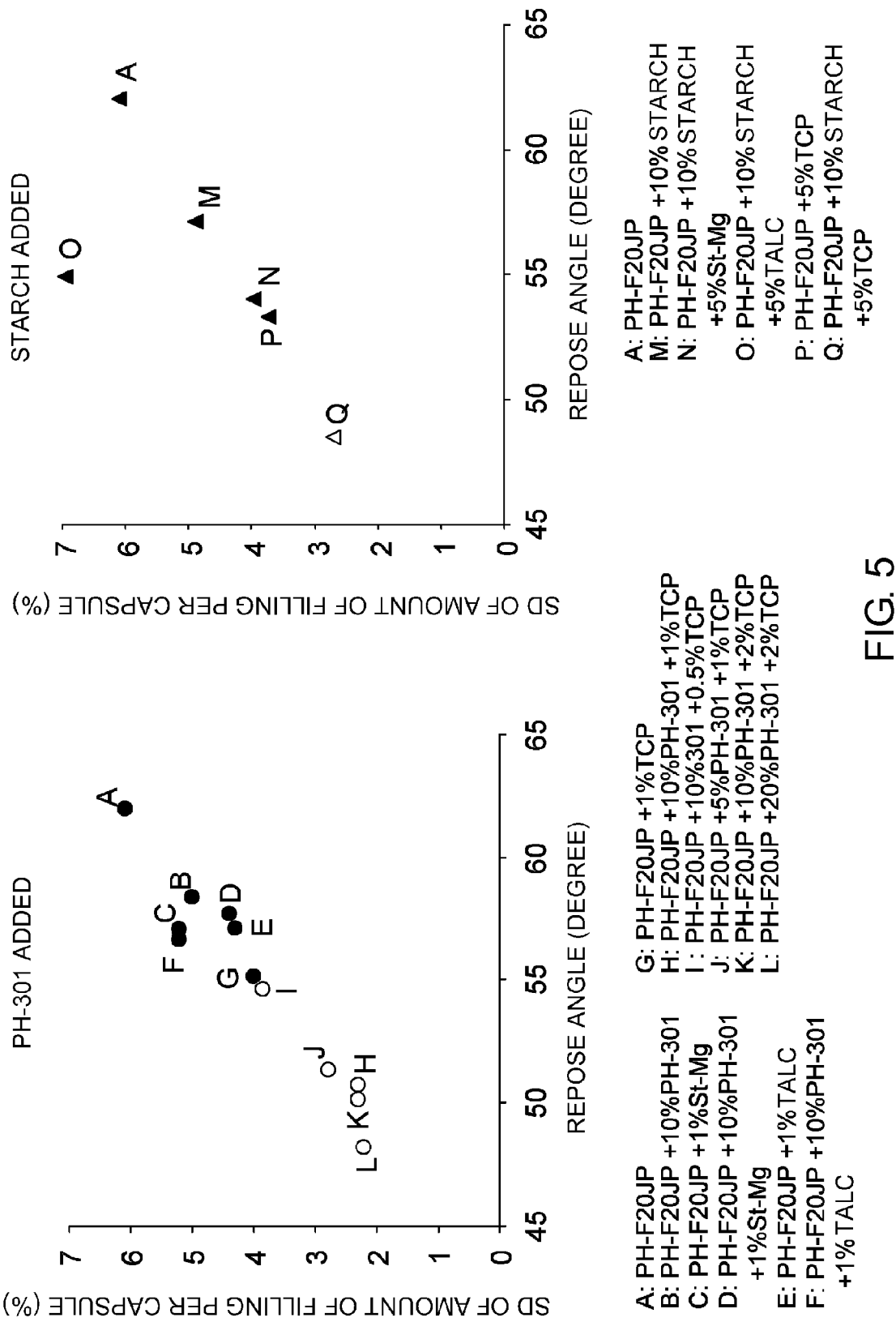

A capsule filling test was conducted to assess whether flowability improvement affects variation in the filling amount per capsule. After striking, various carriers for nasal administration were filled into 50 capsules (gelatin, size-1 capsule) using a manual capsule filling device (a commercially available manual capsule filling machine; Cap-M-Quick™, S.L. Sanderson and Co.), and the amount of filling in each capsule was determined to compare the variations. Table 7 shows the percentages of minimal and maximal filling amounts using the average filling amount for 50 capsules as standard, and the standard deviations (SDs) of the variations in the filling amounts (%) of 50 capsules. FIG. 4 shows filling variations among 50 capsules. FIG. 5 shows the relationship between the angle of repose and the variation in the filling amount per capsule (%).

TABLE 7

Uniformity of the filling amount per capsule

|  | MINIMUM (%) | MAXIMUM (%) | SD |
|---|---|---|---|
| PH-F20JP | 87.1 | 115.0 | 6.1 |
| PH-F20JP + 10% PH-301 | 91.3 | 112.6 | 5.0 |
| PH-F20JP + 1% St-Mg | 90.6 | 109.8 | 5.2 |
| PH-F20JP + 10% PH-301 + 1% St-Mg | 91.8 | 115.3 | 4.4 |
| PH-F20JP + 1% TALC | 91.7 | 109.4 | 4.3 |
| PH-F20JP + 10% PH-301 + 1% TALC | 87.8 | 109.7 | 5.2 |
| PH-F20JP + 1% TCP | 92.1 | 107.8 | 4.0 |
| PH-F20JP + 10% PH-301 + 1% TCP | 95.9 | 104.3 | 2.3 |
| PH-F20JP + 10% PH-301 + 0.5% TCP | 91.7 | 107.4 | 3.9 |
| PH-F20JP + 5% PH-301 + 1% TCP | 90.3 | 104.4 | 2.8 |
| PH-F20JP + 10% PH-301 + 2% TCP | 95.0 | 104.4 | 2.3 |
| PH-F20JP + 20% PH-301 + 1% TCP | 95.7 | 104.5 | 2.2 |
| PH-F20JP + 10% STARCH | 87.8 | 109.7 | 4.9 |
| PH-F20JP + 10% STARCH + 5% St-Mg | 90.1 | 108.9 | 4.0 |
| PH-F20JP + 10% STARCH + 5% TALC | 90.5 | 136.1 | 7.0 |
| PH-F20JP + 5% TCP | 91.4 | 107.8 | 3.9 |
| PH-F20JP + 10% STARCH + 5% TCP | 94.1 | 105.7 | 2.8 |

St-Mg, magnesium stearate;
TALC, talc;
TCP, tribasic calcium phosphate;
PH-F20JP, Ceolus ® PH-F20JP;
PH-301, Ceolus ® PH-301;
STARCH, cornstarch.

As shown in FIG. 4, the variation in the filling amount per capsule was reduced by the combined use of Ceolus® PH-F20JP (Asahi Kasei Chemicals Corporation) as a carrier, either Ceolus® PH-301 (Asahi Kasei Chemicals Corporation) or cornstarch (Merck) as a flowability-enhancing agent, and tribasic calcium phosphate (Taihei Chemical Industrial Co., particles with a diameter of 38 μm or less were selected by sorting) as a fluidizing agent. It was found that the preparation H shown in FIG. 4 could be filled into capsules within the variation range of ±5%.

Alternatively, as shown in FIG. 5, there is a positive correlation between the angle of repose and the variation in the filling amount per capsule (%). Thus, the angle of repose is demonstrated to serve as an indicator for assessing the uniformity in capsule filling.

Next, various nasal preparations containing the drugs listed in Tables 4 and 5 were also tested for the capsule filling according to the same procedure. Table 8 shows data related to the uniformity in capsule filling.

TABLE 8

Uniformity in the filling amount per capsule

|  | DRUG | MINIMUM (%) | MAXIMUM (%) | SD |
|---|---|---|---|---|
| GRANISETRON | EXAMPLE 1 | 96.0 | 102.9 | 2.1 |
|  | COMPARATIVE EXAMPLE 1 | 84.1 | 120.7 | 6.4 |
|  | COMPARATIVE EXAMPLE 2 | 89.3 | 117.5 | 5.0 |
| ONDANSETRON | EXAMPLE 3-1 | 94.5 | 104.9 | 2.5 |
|  | EXAMPLE 3-2 | 95.0 | 106.0 | 2.6 |
|  | COMPARATIVE EXAMPLE 3 | 82.3 | 120.1 | 5.5 |
| MORPHINE | EXAMPLE 4 | 93.7 | 104.4 | 2.4 |
|  | EXAMPLE 5-1 | 95.9 | 103.2 | 2.1 |

TABLE 8-continued

Uniformity in the filling amount per capsule

| DRUG | | MINIMUM (%) | MAXIMUM (%) | SD |
|---|---|---|---|---|
| | EXAMPLE 5-2 | 95.2 | 103.0 | 2.2 |
| | EXAMPLE 6 | 92.0 | 108.4 | 3.2 |
| | COMPARATIVE EXAMPLE 4 | 80.3 | 122.2 | 7.3 |
| | COMPARATIVE EXAMPLE 5 | 87.5 | 117.7 | 5.7 |
| | COMPARATIVE EXAMPLE 6 | 85.1 | 120.3 | 6.3 |
| | COMPARATIVE EXAMPLE 7 | 84.0 | 121.1 | 5.9 |
| FENTANYL | EXAMPLE 7-2 | 95.2 | 104.0 | 2.3 |
| | COMPARATIVE EXAMPLE 8 | 85.9 | 113.5 | 5.3 |
| OXYCODONE | EXAMPLE 8 | 94.1 | 106.5 | 2.9 |
| | COMPARATIVE EXAMPLE 9 | 92.2 | 109.0 | 3.5 |
| SUMATRIPTAN | EXAMPLE 9-1 | 93.9 | 103.0 | 2.4 |
| | EXAMPLE 9-2 | 94.2 | 102.8 | 2.3 |
| | COMPARATIVE EXAMPLE 10-1 | 79.8 | 123.3 | 7.5 |
| | COMPARATIVE EXAMPLE 10-2 | 89.4 | 118.7 | 4.7 |
| BECLOMETASONE | EXAMPLE 10 | 95.3 | 104.8 | 2.2 |
| | COMPARATIVE EXAMPLE 11 | 83.7 | 119.0 | 5.9 |
| KETOTIFEN | EXAMPLE 11 | 96.1 | 103.8 | 2.3 |
| | COMPARATIVE EXAMPLE 12 | 85.9 | 121.3 | 6.2 |
| INSULIN | EXAMPLE 12 | 94.5 | 105.0 | 2.6 |
| | EXAMPLE 14 | 92.1 | 109.9 | 3.3 |
| | COMPARATIVE EXAMPLE 13 | 78.4 | 124.7 | 8.1 |
| | COMPARATIVE EXAMPLE 14 | 83.1 | 117.9 | 7.0 |
| | COMPARATIVE EXAMPLE 15 | 82.3 | 125.3 | 7.8 |
| ZOLMITRIPTAN | EXAMPLE 17 | 95.6 | 103.2 | 2.2 |
| | COMPARATIVE EXAMPLE 18 | 83.2 | 129.7 | 5.9 |

The degree of variation in the filling amount per capsule was evidently smaller in preparations obtained by combining various drugs with Ceolus® PH-F20JP (Asahi Kasei Chemicals Corporation) as a carrier, either Ceolus® PH-301 (Asahi Kasei Chemicals Corporation) or cornstarch (Merck) as a flowability-enhancing agent, and tribasic calcium phosphate (Taihei Chemical Industrial Co., particles with a diameter of 38 μm or less were selected by sorting) as a fluidizing agent. This tendency in capsule filling was the same as that of those carriers of nasal administration shown in Table 7 that did not contain drug.

As described above, due to the improved flowability of powdery preparations, the nasal preparations of the present invention exhibited the effect of markedly improving uniformity in the filling amount per capsule.

Next, carriers containing various flowability-improving components were assessed for flowability by the collapse-slide test.

The collapsing property of piles of accumulated powdery carriers was tested to assess the flowability of powdery carriers using a method different from that used for determining the angle of repose. The test was conducted with the following procedure: powdery carriers were poured into a vessel of a particular volume (7.5-cm height×2.5-cm width×2.5-cm depth) from above, and after striking the powder at the top of the filled vessel, the filing weight (A) was determined. Then, a lateral wall of the vessel was removed and the weight (B) of the powder outflowing from the vessel was determined. The ratio of outflow powder (=B/A×100) was referred to as collapse-slide ratio and used as an indicator of flowability. This method enables one to numerically compare the sliding/outflowing effect of particles of powdery carriers. The ratio serves as an indicator as to whether powdery carriers flow evenly through the flow path of a capsule filling machine and flow evenly into the mortar with a particular volume placed on a rotating plate to determine the filling amount per capsule (see FIG. 6).

The collapse-slide ratios of various carriers (averages in triplicate) are shown in Table 9.

TABLE 9

Ratio of particles collapsed/slid from a vessel

| | MEAN RATIO OF PARTICLES COLLAPSED/SLID (%) | SD |
|---|---|---|
| PH-F20JP | 0.0 | 0.0 |
| PH-F20JP + 10% PH-301 | 0.0 | 0.0 |
| PH-F20JP + 1% St-Mg | 0.0 | 0.0 |
| PH-F20JP + 10% PH-301 + 1% St-Mg | 0.0 | 0.0 |
| PH-F20JP + 1% TALC | 0.0 | 0.0 |
| PH-F20JP + 10% PH-301 + 1% TALC | 11.5 | 3.3 |
| PH-F20JP + 1% TCP | 30.2 | 5.1 |
| PH-F20JP + 10% PH-301 + 1% TCP | 61.5 | 2.5 |
| PH-F20JP + 10% STARCH | 0.0 | 0.0 |
| PH-F20JP + 10% STARCH + 5% St-Mg | 0.0 | 0.0 |
| PH-F20JP + 10% STARCH + 5% TALC | 8.9 | 2.6 |
| PH-F20JP + 10% STARCH + 5% TCP | 40.0 | 5.7 |

As shown in Table 9, collapsing/sliding from the vessel was observed only in the preparations containing tribasic calcium phosphate, among cases where Ceolus® PH-F20JP (Asahi Kasei Chemicals Corporation) as a carrier, and any one of magnesium stearate, talc, and tribasic calcium phosphate as a fluidizing agent were added. Furthermore, collapsing/sliding from the vessel was also observed when talc or tribasic calcium phosphate was added, among cases where any one of magnesium stearate, talc, and tribasic calcium phosphate was added as a fluidizing agent to a mixture of Ceolus® PH-F20JP (Asahi Kasei Chemicals Corporation) as a carrier and either Ceolus® PH-301 (Asahi Kasei Chemicals Corporation) or cornstarch (Merck) as a flowability-enhancing agent. The preparations containing tribasic calcium phosphate as an additive were demonstrated to significantly more easily collapse and slide than preparations containing talc as an additive.

Furthermore, various nasal preparations containing the drugs listed in Tables 4 and 5 were also assessed for the collapsing/sliding property according to the same procedure. The collapse-slide ratios (averages in triplicate) are shown in Table 10.

TABLE 10

Ratio of particles collapsed/slid from a vessel

| DRUG | | MEAN RATIO OF PARTICLES COLLAPSED/SLID (%) | SD |
|---|---|---|---|
| GRANISETRON | EXAMPLE 1 | 63.1 | 2.1 |
| | COMPARATIVE EXAMPLE 1 | 0.0 | 0.0 |
| | COMPARATIVE EXAMPLE 2 | 0.0 | 0.0 |
| ONDANSETRON | EXAMPLE 3-1 | 60.8 | 1.7 |
| | EXAMPLE 3-2 | 58.7 | 1.0 |
| | COMPARATIVE EXAMPLE 3 | 0.0 | 0.0 |

TABLE 10-continued

Ratio of particles collapsed/slid from a vessel

| DRUG | | MEAN RATIO OF PARTICLES COLLAPSED/SLID (%) | SD |
|---|---|---|---|
| MORPHINE | EXAMPLE 4 | 61.0 | 1.8 |
| | EXAMPLE 5-1 | 65.9 | 2.6 |
| | EXAMPLE 5-2 | 69.8 | 1.3 |
| | EXAMPLE 6 | 28.7 | 3.4 |
| | COMPARATIVE EXAMPLE 4 | 0.0 | 0.0 |
| | COMPARATIVE EXAMPLE 5 | 0.0 | 0.0 |
| | COMPARATIVE EXAMPLE 6 | 7.1 | 3.0 |
| | COMPARATIVE EXAMPLE 7 | 0.0 | 0.0 |
| FENTANYL | EXAMPLE 7-2 | 70.1 | 3.0 |
| | COMPARATIVE EXAMPLE 8 | 0.0 | 0.0 |
| OXYCODONE | EXAMPLE 8 | 64.1 | 2.7 |
| | COMPARATIVE EXAMPLE 9 | 0.0 | 0.0 |
| SUMATRIPTAN | EXAMPLE 9-1 | 61.0 | 2.5 |
| | EXAMPLE 9-2 | 62.5 | 1.2 |
| | COMPARATIVE EXAMPLE 10-1 | 0.0 | 0.0 |
| | COMPARATIVE EXAMPLE 10-2 | 0.0 | 0.0 |
| BECLOMETASONE | EXAMPLE 10 | 65.0 | 2.9 |
| | COMPARATIVE EXAMPLE 11 | 0.0 | 0.0 |
| KETOTIFEN | EXAMPLE 11 | 64.6 | 3.2 |
| | COMPARATIVE EXAMPLE 12 | 0.0 | 0.0 |
| INSULIN | EXAMPLE 12 | 67.7 | 2.3 |
| | EXAMPLE 14 | 24.3 | 3.9 |
| | COMPARATIVE EXAMPLE 13 | 0.0 | 0.0 |
| | COMPARATIVE EXAMPLE 14 | 0.0 | 0.0 |
| | COMPARATIVE EXAMPLE 15 | 10.2 | 2.6 |
| ZOLMITRIPTAN | EXAMPLE 17 | 63.1 | 2.0 |
| | COMPARATIVE EXAMPLE 18 | 0.0 | 0.0 |

Preparations obtained by combining various drugs with Ceolus® PH-F20JP (Asahi Kasei Chemicals Corporation) as a carrier, either Ceolus® PH-301 (Asahi Kasei Chemicals Corporation) or cornstarch (Merck) as a flowability-enhancing agent, and tribasic calcium phosphate (Taihei Chemical Industrial Co., particles with a diameter of 38 µm or less were selected by sorting) as a fluidizing agent were demonstrated to collapse and slide much more easily.

As described above, the nasal preparations of the present invention were demonstrated to have markedly improved collapsing/sliding property related to flowability.

Next, carriers containing various flowability-improving components were assessed for their spray efficiency by a nasal device.

It is necessary to use a nasal device or such to spray a capsule powdery preparation into a nasal cavity, which is the administration site. Since the flowability of powdery preparations is an important factor that determines the amount of spray by a nasal device and the uniformity of spraying, the efficiencies of spray by a nasal device were compared among powdery carriers. The commercially available Publizer® (Teijin Pharma) and Fit-lizer® (Bioactis, Ltd.), which was under development, were used for assessment as nasal devices for capsule powdery preparations.

Various carriers (10, 25, or 50 mg) were filled with high accuracy into size-2 HPMC capsules, and the pump component of a nasal device was pressed with a constant external pressure (30 kPa). The spraying amount was determined based on the change in the weight of the nasal device. The pump component was pressed five times consecutively for Publizer®, and once for Fit-lizer®. In order to press the pump component of a nasal device with a constant pressure, a spray device that uses an air cylinder for pressing was prepared and used in the test. The minimal pressure when a healthy woman presses the pump is adopted as the external pressure (30 kPa) for pressing the pump component.

Tables 11 and 12 show average spraying efficiencies of spraying and their standard deviations (SDs) for 10 capsules filled with each of the various powder carriers when they are sprayed using a nasal device. Corresponding diagrams are shown in FIGS. 7-1 and 7-2.

TABLE 11

Efficiency of spray by the Publizer nasal device

| NASAL DEVICE: PUBLIZER | CAPSULE FILLING AMOUNT (mg/CAPSULE) | MEAN SPRAYING EFFICIENCY (%) | SD |
|---|---|---|---|
| PH-F20JP | 10 | 64.2 | 9.6 |
| | 25 | 54.9 | 12.2 |
| | 50 | 57.0 | 10.4 |
| PH-F20JP + 10% PH-301 | 10 | 69.9 | 10.0 |
| | 25 | 56.7 | 9.6 |
| | 50 | 58.4 | 7.3 |
| PH-F20JP + 10% PH-301 + 1% St-Mg | 10 | 70.5 | 7.8 |
| | 25 | 62.8 | 8.7 |
| | 50 | 58.0 | 6.7 |
| PH-F20JP + 10% PH-301 + 1% TALC | 10 | 66.7 | 14.0 |
| | 25 | 63.2 | 8.2 |
| | 50 | 57.8 | 8.1 |
| PH-F20JP + 1% TCP | 10 | 71.2 | 8.0 |
| | 25 | 69.7 | 8.0 |
| | 50 | 66.0 | 8.1 |
| PH-F20JP + 10% PH-301 + 1% TCP | 10 | 78.9 | 3.4 |
| | 25 | 82.7 | 5.2 |
| | 50 | 76.0 | 7.7 |
| PH-F20JP + 10% STARCH | 25 | 57.8 | 9.7 |
| PH-F20JP + 10% STARCH + 5% TCP | 25 | 72.9 | 5.2 |

St-Mg, magnesium stearate;
TALC, talc;
TCP, tribasic calcium phosphate;
PH-F20JP, Ceolus ® PH-F20JP;
PH-301, Ceolus ® PH-301;
STARCH, cornstarch.

TABLE 12

Efficiency of spray by a nasal device (Fit-lizer)

| NASAL DEVICE: FIT-LIZER | CAPSULE FILLING AMOUNT (mg/CAPSULE) | MEAN SPRAYING EFFICIENCY (%) | SD |
|---|---|---|---|
| PH-F20JP | 50 | 91.0 | 4.7 |
| PH-F20JP + 10% PH-301 | 50 | 92.3 | 2.9 |
| PH-F20JP + 10% PH-301 + 1% St-Mg | 50 | 92.5 | 2.1 |
| PH-F20JP + 10% PH-301 + 1% TALC | 50 | 92.7 | 2.6 |
| PH-F20JP + 1% TCP | 50 | 93.2 | 2.5 |
| PH-F20JP + 10% PH-301 + 1% TCP | 50 | 95.2 | 0.7 |

St-Mg, magnesium stearate;
TALC, talc;
TCP, tribasic calcium phosphate;
PH-F20JP, Ceolus ® PH-F20JP;
PH-301, Ceolus ® PH-301.

As clearly seen in Tables 11 and 12, and FIGS. 7-1 and 8, the amount of the carrier of PH-F20JP plus PH-301 and tribasic calcium phosphate sprayed from a nasal device was demonstrated to be statistically significantly higher than that of other carriers. Furthermore, as shown in FIG. 7-2, the spraying efficiency for the carrier of PH-F20JP plus PH-301 and tribasic calcium phosphate was found to be stably high, regardless of the changes in the amount of preparation in a capsule. In addition, as shown in FIG. 7-2, the amount of the carrier of PH-F20JP plus starch and tribasic calcium phosphate sprayed from a nasal device was also demonstrated to be statistically significantly higher than that of other carriers.

Various nasal preparations containing the drugs listed in Tables 4 and 5 were also assessed for the efficiency of spray by the nasal device.

Preparations (25 mg) were filled with high accuracy into size-2 HPMC capsules, and the pump component of Publizer® was pressed five times consecutively with a constant external pressure (30 kPa). The spraying amount was determined based on the change in the weight of the nasal device. A spray device that uses an air cylinder for pressing the pump component of the nasal device was prepared and used in the test. Table 13 shows average spraying efficiencies for 10 capsules and their standard deviations (SDs).

ity-enhancing agent, and tribasic calcium phosphate (Taihei Chemical Industrial Co.; particles with a diameter of 38 μm or less were selected by sorting) as a fluidizing agent.

As described above, the nasal preparations of the present invention showed increased uniformity and amount sprayed by the nasal device, and the spraying efficiency was constant regardless of the amount of preparation in a capsule. Accordingly, the nasal preparations of the present invention enable accurate dosages to be administered into a nasal cavity.

The dosage of nasal preparation administered into a nasal cavity varies due to variations in the amount of preparation in a capsule and the amount sprayed by a device. In that regard, the nasal preparations of the present invention improved uniformity in the amount filled in a capsule and the amount sprayed by a nasal device, and the improved uniformity is very important in terms of achieving steady and safe treatment by using adequate doses of drug.

Next, animal tests were performed to assess the preparations of the present invention with improved flowability for the effect on nasal drug absorption.

Using a nasal device (Fit-lizer®, Bioactis, Ltd.), the nasal granisetron preparations prepared as described in Examples 1 and 2, and Comparative Example 1 were administered at a

TABLE 13

Efficiency of spray by the Publizer nasal device

| NASAL DEVICE: PUBLIZER | | CAPSULE FILLING AMOUNT (mg/CAPSULE) | MEAN SPRAYING EFFICIENCY (%) | SD |
|---|---|---|---|---|
| GRANISETRON | EXAMPLE 1 | 25 | 79.1 | 3.4 |
| | COMPARATIVE EXAMPLE 1 | 25 | 52.4 | 10.4 |
| | COMPARATIVE EXAMPLE 2 | 25 | 56.4 | 8.7 |
| ONDANSETRON | EXAMPLE 3-1 | 25 | 77.5 | 4.8 |
| | EXAMPLE 3-2 | 25 | 79.4 | 4.5 |
| | COMPARATIVE EXAMPLE 3 | 25 | 51.1 | 10.7 |
| MORPHINE | EXAMPLE 4 | 25 | 78.3 | 3.6 |
| | EXAMPLE 5-1 | 25 | 80.1 | 2.6 |
| | EXAMPLE 5-2 | 25 | 83.9 | 2.5 |
| | EXAMPLE 6 | 25 | 73.8 | 6.0 |
| | COMPARATIVE EXAMPLE 4 | 25 | 48.1 | 10.0 |
| | COMPARATIVE EXAMPLE 5 | 25 | 50.5 | 7.9 |
| | COMPARATIVE EXAMPLE 6 | 25 | 46.8 | 8.0 |
| | COMPARATIVE EXAMPLE 7 | 25 | 47.8 | 9.2 |
| FENTANYL | EXAMPLE 7-2 | 25 | 82.3 | 3.8 |
| | COMPARATIVE EXAMPLE 8 | 25 | 56.9 | 10.2 |
| OXYCODONE | EXAMPLE 8 | 25 | 77.4 | 4.7 |
| | COMPARATIVE EXAMPLE 9 | 25 | 64.0 | 9.1 |
| SUMATRIPTAN | EXAMPLE 9-1 | 25 | 83.5 | 3.5 |
| | EXAMPLE 9-2 | 25 | 83.8 | 2.6 |
| | COMPARATIVE EXAMPLE 10-1 | 25 | 55.5 | 10.4 |
| | COMPARATIVE EXAMPLE 10-2 | 25 | 58.2 | 8.0 |
| BECLOMETASONE | EXAMPLE 10 | 25 | 81.3 | 5.1 |
| | COMPARATIVE EXAMPLE 11 | 25 | 52.5 | 10.5 |
| KETOTIFEN | EXAMPLE 11 | 25 | 80.2 | 4.6 |
| | COMPARATIVE EXAMPLE 12 | 25 | 53.3 | 10.1 |
| INSULIN | EXAMPLE 12 | 25 | 79.7 | 3.4 |
| | EXAMPLE 14 | 25 | 74.1 | 6.3 |
| | COMPARATIVE EXAMPLE 13 | 25 | 50.7 | 10.4 |
| | COMPARATIVE EXAMPLE 14 | 25 | 51.1 | 10.0 |
| | COMPARATIVE EXAMPLE 15 | 25 | 48.6 | 9.2 |
| HMG | EXAMPLE 15 | 25 | 80.6 | 3.2 |
| | COMPARATIVE EXAMPLE 16 | 25 | 49.6 | 9.8 |
| PTH(1-34) | EXAMPLE 16 | 25 | 83.3 | 3.0 |
| | COMPARATIVE EXAMPLE 17-1 | 25 | 54.7 | 9.8 |
| | COMPARATIVE EXAMPLE 17-2 | 25 | 50.9 | 9.0 |
| ZOLMITRIPTAN | EXAMPLE 17 | 25 | 79.5 | 3.7 |
| | COMPARATIVE EXAMPLE 18 | 25 | 56.3 | 11.3 |

It was demonstrated that the amount sprayed by the nasal device was increased and the degree of variation was reduced when preparations were produced by combining various drugs with Ceolus® PH-F20JP (Asahi Kasei Chemicals Corporation) as a carrier, either Ceolus® PH-301 (Asahi Kasei Chemicals Corporation) or cornstarch (Merck) as a flowability-enhancing agent, and tribasic calcium phosphate (Taihei Chemical Industrial Co.; particles with a diameter of 38 μm or less were selected by sorting) as a fluidizing agent.

dose of 50 mg/head (equivalent to the granisetron dose of 2 mg/head) into the right nasal cavities of male cynomolgus monkeys (body weight: 4.62 to 7.10 kg). Nearly the full doses of the preparations were administered to the animals by pressing the pump of the nasal device until the full preparations were sprayed.

Blood was collected from the femoral vein 5, 10, 30, 60, 120, 240, and 480 minutes after administration, and plasma granisetron concentration was determined by the HPLC method. FIG. 9 shows a time course of plasma granisetron concentration. Table 14 shows plasma granisetron concentrations and pharmacokinetic parameters.

TABLE 14

Plasma granisetron concentration

| GRANISETRON | | TIME (MIN)/PLASMA CONCENTRATION (ng/mL) | | | | | | | PK PARAMETER | | |
|---|---|---|---|---|---|---|---|---|---|---|---|
| | | 5 | 10 | 30 | 60 | 120 | 240 | 480 | $T_{max}$ (min) | $C_{max}$ (ng/mL) | $AUC_{0-480}$ (ng · min/mL) |
| EXAMPLE 1 | ANIMAL 1 (7.00 kg) | 23.8 | 44.6 | 99.2 | 53.6 | 34.6 | 9.5 | N.D. | 30 | 99.2 | 10392.5 |
| | ANIMAL 2 (5.99 kg) | 17.7 | 68.2 | 58.2 | 47.3 | 14.2 | 8.1 | N.D. | 10 | 68.2 | 7788.5 |
| | MEAN (6.50 kg) | 20.8 | 56.4 | 78.7 | 50.5 | 24.4 | 8.8 | N.D. | 20 | 83.7 | 9090.5 |
| EXAMPLE 2 | ANIMAL 1 (5.77 kg) | 24.1 | 44.8 | 53.5 | 46.3 | 26.0 | 12.8 | 5.0 | 30 | 53.5 | 9345.5 |
| | ANIMAL 2 (7.10 kg) | 49.6 | 61.9 | 48.3 | 47.2 | 19.5 | 13.9 | N.D. | 10 | 61.9 | 8610.3 |
| | MEAN (6.44 kg) | 36.9 | 53.4 | 50.9 | 46.8 | 22.8 | 13.4 | N.D. | 20 | 57.7 | 8977.9 |
| COMPARATIVE EXAMPLE 1 | ANIMAL 1 (6.51 kg) | 14.2 | 37.5 | 58.9 | 47.4 | 18.8 | 6.4 | N.D. | 30 | 58.9 | 6989.3 |
| | ANIMAL 2 (4.62 kg) | 24.6 | 92.4 | 83.8 | 54.4 | 21.8 | 9.0 | N.D. | 10 | 92.4 | 9403.0 |
| | MEAN (5.57 kg) | 19.4 | 65.0 | 71.4 | 50.9 | 20.3 | 7.7 | N.D. | 20 | 75.7 | 8196.1 |

N.D.: below the limit of determination (<5 ng/mL)
Tmax: time required to reach the maximal blood drug concentration
Cmax: maximal blood drug concentration
AUC: area under the blood drug concentration vs. time curve There was no difference in the blood granisetron concentration between Examples 1 and 2, and Comparative Example 1. Thus, the preparations of the present invention which have improved flowability were demonstrated to have no effect on the nasal absorption of granisetron.

Using a nasal device (Fit-lizer®, Bioactis, Ltd.), the nasal morphine preparations obtained as described in Examples 4 to 6, and Comparative Example 4 were administered at a dose of 50 mg/head (equivalent to the morphine dose of 4 mg/head) into the right nasal cavities of male cynomolgus monkeys (body weight: 4.95 to 6.97 kg). Nearly the full doses of the preparations were administered to the animals by pressing the pump of the nasal device until the full preparations were sprayed.

Blood was collected from the femoral vein 5, 10, 20, 30, 60, 120, and 480 minutes after administration, and plasma morphine concentration was determined by the HPLC method. FIG. 10 shows a time course of plasma morphine concentration. Table 15 shows plasma morphine concentrations and pharmacokinetic parameters.

TABLE 15

Plasma morphine concentration

| MORPHINE | | TIME (MIN)/PLASMA CONCENTRATION (ng/mL) | | | | | | | PK PARAMETER | | |
|---|---|---|---|---|---|---|---|---|---|---|---|
| | | 5 | 10 | 20 | 30 | 60 | 120 | 240 | $T_{max}$ (min) | $C_{max}$ (ng/mL) | $AUC_{0-240}$ (ng · min/mL) |
| EXAMPLE 4 | ANIMAL 1 (5.84 kg) | 143.3 | 153.5 | 129.9 | 93.5 | 51.0 | 32.3 | 10.6 | 10 | 153.5 | 10877.1 |
| | ANIMAL 2 (6.63 kg) | 146.0 | 168.0 | 110.9 | 83.6 | 42.6 | 36.9 | 12.9 | 10 | 168.0 | 10783.2 |
| | MEAN (6.24 kg) | 144.7 | 160.8 | 120.4 | 88.6 | 46.8 | 34.6 | 11.7 | 10 | 160.8 | 10830.1 |
| EXAMPLE 5 | ANIMAL 1 (5.87 kg) | 130.0 | 110.1 | 51.9 | 46.9 | 72.4 | 47.5 | N.D. | 5 | 130.0 | 10465.8 |
| | ANIMAL 2 (5.96 kg) | 226.8 | 169.9 | 124.0 | 99.2 | 44.3 | 21.6 | N.D. | 5 | 226.8 | 9569.8 |
| | MEAN (5.92 kg) | 178.4 | 140.0 | 88.0 | 73.1 | 58.4 | 34.6 | N.D. | 5 | 178.4 | 10017.8 |
| EXAMPLE 6 | ANIMAL 1 (5.80 kg) | 168.4 | 150.7 | 94.4 | 79.8 | 59.4 | 22.5 | N.D. | 5 | 168.4 | 9210.3 |
| | ANIMAL 2 (6.97 kg) | 220.9 | 157.8 | 122.2 | 112.2 | 79.9 | 48.4 | N.D. | 5 | 220.9 | 13705.5 |

TABLE 15-continued

Plasma morphine concentration

| MORPHINE | | TIME (MIN)/PLASMA CONCENTRATION (ng/mL) | | | | | | | PK PARAMETER | | |
|---|---|---|---|---|---|---|---|---|---|---|---|
| | | 5 | 10 | 20 | 30 | 60 | 120 | 240 | $T_{max}$ (min) | $C_{max}$ (ng/mL) | $AUC_{0-240}$ (ng·min/mL) |
| | MEAN (6.39 kg) | 194.7 | 154.3 | 108.3 | 96.0 | 69.7 | 35.5 | N.D. | 5 | 194.7 | 11457.9 |
| COMPARATIVE EXAMPLE 4 | ANIMAL 1 (5.74 kg) | 143.7 | 172.9 | 101.8 | 79.7 | 45.2 | — | N.D. | 10 | 172.9 | 9987.0 |
| | ANIMAL 2 (4.94 kg) | 82.5 | 120.2 | 104.4 | 120.7 | 89.3 | — | 15.8 | 10 | 120.2 | 15572.2 |
| | MEAN (5.34 kg) | 113.1 | 146.5 | 103.1 | 100.2 | 67.2 | — | 7.9 | 10 | 146.6 | 12779.6 |
| COMPARATIVE EXAMPLE 5 | ANIMAL 1 (5.94 kg) | 86.9 | 78.4 | 67.6 | 66.6 | 42.0 | 20.7 | N.D | 5 | 86.9 | 6783.5 |
| | ANIMAL 2 (6.48 kg) | 95.9 | 109.0 | 73.1 | 59.5 | 40.7 | 21.1 | N.D | 10 | 109.0 | 6948.5 |
| | MEAN (6.21 kg) | 91.4 | 93.7 | 70.4 | 63.1 | 41.4 | 20.9 | N.D | 7.5 | 98.0 | 6866.0 |

There was no difference in the blood morphine concentration between Examples 4 to 6, and Comparative Example 4. Thus, the preparations of the present invention which have improved flowability were demonstrated to have no effect on the nasal absorption of morphine. Furthermore, regarding the plasma morphine concentration after administration of the magnesium stearate-containing preparation of Comparative Example 5, the maximal blood concentration (Cmax) decreased down to 50% and the area under the blood concentration vs. time curve decreased down to 54%, as compared with those of other Examples and Comparative Example 4. This suggests that the structural lipid-soluble portion of magnesium stearate, which is a fatty acid, inhibits the affinity of drug to nasal mucus when it is in contact and as a result, the drug absorption was decreased.

Using a nasal device (Fit-lizer®, Bioactis, Ltd.), the nasal sumatriptan preparations prepared as described in Example 9 and Comparative Example 10 were administered at a dose of 50 mg/head (equivalent to the sumatriptan dose of 6 mg/head) into the right nasal cavities of male cynomolgus monkeys (body weight: 5.86 to 6.79 kg). Nearly the full doses of the preparations were administered to the animals by pressing the pump of the nasal device until the full preparations were sprayed.

Blood was collected from the femoral vein 15, 30, 60, 90, 180, 240, and 480 minutes after administration, and plasma sumatriptan concentration was determined by the HPLC method. FIG. 11 shows a time course of plasma sumatriptan concentration. Table 16 shows plasma sumatriptan concentrations and pharmacokinetic parameters.

TABLE 16

Plasma sumatriptan concentration

| SUMATRIPTAN | | TIME (MIN)/PLASMA CONCENTRATION (ng/mL) | | | | | | | PK PARAMETER | | |
|---|---|---|---|---|---|---|---|---|---|---|---|
| | | 15 | 30 | 60 | 90 | 180 | 240 | 480 | $T_{max}$ (min) | $C_{max}$ (ng/mL) | $AUC_{0-480}$ (ng·min/mL) |
| EXAMPLE 9 | ANIMAL 1 (6.79 kg) | 314.8 | 177.7 | 139.3 | 78.0 | 45.2 | 32.7 | 10.7 | 15 | 314.8 | 27158.3 |
| | ANIMAL 2 (6.61 kg) | 203.9 | 111.6 | 81.3 | 70.3 | 44.5 | 41.6 | 15.4 | 15 | 203.9 | 23652.0 |
| | MEAN (6.70 kg) | 259.4 | 144.7 | 110.3 | 74.2 | 44.9 | 37.2 | 13.1 | 15 | 259.4 | 25405.1 |
| COMPARATIVE EXAMPLE 10-1 | ANIMAL 1 (5.86 kg) | 317.8 | 307.3 | 191.5 | 130.2 | 100.6 | 68.9 | 26.3 | 15 | 317.8 | 46274.3 |
| | ANIMAL 2 (5.88 kg) | 370.5 | 191.3 | 114.0 | 75.0 | 49.6 | 35.3 | 9.8 | 15 | 370.5 | 27972.8 |
| | MEAN (5.87 kg) | 344.2 | 249.3 | 152.8 | 102.6 | 75.1 | 52.1 | 18.1 | 15 | 344.2 | 37123.5 |

Tmax: time required to reach the maximal blood drug concentration
Cmax: maximal blood drug concentration
AUC: area under the blood drug concentration vs. time curve Regarding the blood sumatriptan concentrations determined in Example 9 and Comparative Example 10-1, there was no difference in absorption between the two when considering the difference in the distribution volume due to the weight difference between the animals. Thus, the preparations of the present invention which have improved flowability were demonstrated to have no effect on the nasal absorption of sumatriptan.

Using a nasal device (Fit-lizer®, Bioactis, Ltd.), the nasal HMG preparations prepared as described in Example 15 and Comparative Example 16 were administered at a dose of 50 mg/head (equivalent to the FSH dose of 50 U/head) into the right nasal cavities of male cynomolgus monkeys (body weight: 5.61 to 6.91 kg). Nearly the full doses of the preparations were administered to the animals by pressing the pump of the nasal device until the full preparations were sprayed.

Blood was collected from the femoral vein 0.5, 1, 2, 4, 6, 12, and 24 hours after administration, and serum FSH concentration was determined by EIA (IBL Co.). FIG. 12 shows a time course of serum FSH concentration. Table 17 shows serum FSH concentrations and pharmacokinetic parameters.

and Comparative Example 17 were administered at a dose of 50 mg/head (equivalent to the PTH(1-34) dose of 120 μg/head) into the right nasal cavities of male cynomolgus monkeys (body weight: 5.97 to 6.74 kg). The nearly whole contents of the preparations were administered to the animals by pressing the pump of the nasal device until the whole amounts of preparations were sprayed.

TABLE 17

Serum FSH concentration

| | | TIME (HR)/SERUM CONCENTRATION (mU/mL) | | | | | | | $T_{max}$ | $C_{max}$ | $AUC_{0-24}$ |
|---|---|---|---|---|---|---|---|---|---|---|---|
| | FSH | 0.5 | 1 | 2 | 4 | 6 | 12 | 24 | (min) | (mU/mL) | (mU · min/mL) |
| EXAMPLE 15 | ANIMAL 1 (5.61 kg) | 1.5 | 3.3 | 5.0 | 6.5 | 6.6 | 5.8 | 2.8 | 6 | 6.6 | 7173.0 |
| | ANIMAL 2 (6.70 kg) | 2.8 | 4.4 | 5.9 | 6.5 | 5.9 | 4.7 | 2.8 | 4 | 6.5 | 6545.7 |
| | MEAN (6.16 kg) | 2.2 | 3.9 | 5.5 | 6.5 | 6.2 | 5.3 | 2.8 | 5 | 6.6 | 6859.4 |
| COMPARATIVE EXAMPLE 16 | ANIMAL 1 (5.72 kg) | 0.0 | 3.0 | 5.5 | 8.1 | 7.4 | 5.8 | 3.0 | 4 | 8.1 | 7575.3 |
| | ANIMAL 2 (6.91 kg) | 1.4 | 3.3 | 4.2 | 5.0 | 4.6 | 3.7 | 1.6 | 4 | 5.0 | 4827.3 |
| | MEAN (6.32 kg) | 0.7 | 3.1 | 4.8 | 6.5 | 6.0 | 4.7 | 2.3 | 4 | 6.6 | 6201.3 |

There was no difference in the blood FSH concentration between Example 15 and Comparative Example 16. Thus, the preparations of the present invention which have improved flowability were demonstrated to have no effect on the nasal absorption of FSH.

Using a nasal device (Fit-lizer®, Bioactis, Ltd.), the nasal PTH(1-34) preparations prepared as described in Example 16

Blood was collected from the femoral vein 5, 10, 20, 30, 40, 60, and 90 minutes after administration, and the serum PTH (1-34) concentration was determined by EIA (Peninsula Laboratories). FIG. 13 shows a time course of serum PTH(1-34) concentration. Table 18 shows serum PTH(1-34) concentrations and pharmacokinetic parameters.

TABLE 18

Serum PTH(1-34) concentration

| | | TIME (MIN)/SERUM CONCENTRATION (ng/mL) | | | | | | | $T_{max}$ | $C_{max}$ | $AUC_{0-90}$ |
|---|---|---|---|---|---|---|---|---|---|---|---|
| | PTH(1-34) | 5 | 10 | 20 | 30 | 40 | 60 | 90 | (min) | (ng/mL) | (ng · min/mL) |
| EXAMPLE 16 | ANIMAL 1 (6.74 kg) | 7.9 | 16.7 | 12.6 | 5.7 | 2.5 | 1.0 | 0.7 | 10 | 16.7 | 420.8 |
| | ANIMAL 2 (6.62 kg) | 12.4 | 20.5 | 9.2 | 3.7 | 1.6 | 0.5 | 0.3 | 10 | 20.5 | 385.8 |
| | MEAN (6.68 kg) | 10.2 | 18.6 | 10.9 | 4.7 | 2.1 | 0.8 | 0.5 | 10 | 18.6 | 403.3 |
| COMPARATIVE EXAMPLE 17-1 | ANIMAL 1 (6.65 kg) | 2.7 | 2.8 | 9.9 | 15.7 | 7.1 | 2.3 | 1.1 | 30 | 15.7 | 471.0 |
| | ANIMAL 2 (5.97 kg) | 3.4 | 6.7 | 16.8 | 8.9 | 5.4 | 1.7 | 0.8 | 20 | 16.8 | 459.8 |
| | MEAN (6.31 kg) | 3.1 | 4.8 | 13.4 | 12.3 | 6.3 | 2.0 | 1.0 | 25 | 16.3 | 465.4 |
| COMPARATIVE EXAMPLE 17-2 | ANIMAL 1 (6.86 kg) | 0.4 | 0.8 | 0.7 | 0.6 | 0.4 | 0.3 | 0.2 | 10 | 0.8 | 37.5 |
| | ANIMAL 2 (6.59 kg) | 0.9 | 0.9 | 0.6 | 0.5 | 0.4 | 0.2 | 0.2 | 5 | 0.9 | 36.3 |
| | MEAN (6.73 kg) | 0.7 | 0.9 | 0.7 | 0.6 | 0.4 | 0.3 | 0.2 | 7.5 | 0.9 | 36.9 |

There was no marked difference in the absorption efficiency between Example 16 and Comparative Example 17-1. As can be seen from the difference in the Tmax value (time required to reach the maximal blood concentration), the absorption of PTH(1-34) in Example 16 was accelerated. This suggests that the dispersibility of the nasal preparation improved and the intranasal distribution of the preparation sprayed by the nasal device became broad as a result of improved flowability, and thus the rate of PTH(1-34) absorption from nasal mucosa was increased. Furthermore, regarding the serum PTH(1-34) concentration after administration of the magnesium stearate-containing preparation of Example 17-2, the maximal blood concentration (Cmax) and the area under the blood concentration vs. time curve markedly decreased down to 5% and 8%, respectively, in comparison with Example 16 and Comparative Example 17-1. This suggests that the structural lipid-soluble portion of magnesium stearate, which is a fatty acid, inhibits the affinity of drug to nasal mucus when it is in contact and as a result, the drug absorption was decreased.

Next, using a nasal device (Fit-lizer®, Bioactis, Ltd.), the nasal fentanyl preparations prepared as described in Example 7-2 and Comparative Example 8 were administered at a dose of 25 mg/head (equivalent to the fentanyl dose of 100 μg/head) into the right nasal cavities of male cynomolgus monkeys (body weight of 6.41 to 7.26 kg). Nearly the full doses of the preparations were administered to the animals by pressing the pump of the nasal device until the full preparations were sprayed.

Blood was collected from the femoral vein 2, 5, 10, 15, 30, 60, 120, 240, and 480 minutes after administration, and plasma fentanyl concentration was determined by the LC-MS/MS method. FIG. 14 shows a time course of plasma fentanyl concentration. Table 9 shows plasma fentanyl concentrations and pharmacokinetic parameters.

TABLE 19

Plasma fentanyl concentration

| FENTANYL | | TIME (MIN)/PLASMA CONCENTRATION (ng/mL) | | | | | | | | | $T_{max}$ (min) | $C_{max}$ (ng/mL) | $AUC_{0-480}$ (ng·min/mL) |
|---|---|---|---|---|---|---|---|---|---|---|---|---|---|
| | | 2 | 5 | 10 | 15 | 30 | 60 | 120 | 240 | 480 | | | |
| EXAMPLE 7-2 | ANIMAL 1 (6.61 kg) | 0.53 | 2.61 | 3.96 | 5.21 | 5.32 | 3.93 | 1.83 | 0.71 | 0.24 | 30 | 5.32 | 701.5 |
| | ANIMAL 2 (7.26 kg) | 0.67 | 1.70 | 1.61 | 4.83 | 3.76 | 2.95 | 1.60 | 0.82 | 0.18 | 15 | 4.83 | 595.4 |
| | MEAN (6.94 kg) | 0.60 | 2.16 | 2.79 | 5.02 | 4.54 | 3.44 | 1.72 | 0.77 | 0.21 | 22.5 | 5.08 | 648.5 |
| COMPARATIVE EXAMPLE 8 | ANIMAL 1 (6.40 kg) | 0.31 | 1.99 | 2.87 | 4.78 | 4.24 | 3.68 | 1.73 | 0.82 | 0.20 | 15 | 4.78 | 659.2 |
| | ANIMAL 2 (7.10 kg) | 0.45 | 2.51 | 3.10 | 4.35 | 4.00 | 3.23 | 1.49 | 0.63 | 0.18 | 15 | 4.35 | 574.6 |
| | MEAN (6.75 kg) | 0.38 | 2.25 | 2.99 | 4.56 | 4.12 | 3.46 | 1.61 | 0.73 | 0.19 | 15 | 4.57 | 616.9 |

There was no difference in the blood fentanyl concentration between Example 7-2 and Comparative Example 8. Thus, the preparations of the present invention which have improved flowability were demonstrated to have no effect on the nasal absorption of fentanyl.

Industrial Applicability

Nasal preparations containing a complex of a physiologically active substance and a flowability-improving component of the present invention have superior flowability and are useful for nasal administrations. Furthermore, there is no difference in the nasal absorption between when a preparation of the present invention is nasally administered, and when a preparation that uses only the first crystalline cellulose as a carrier and contains the same amount of a physiologically active substance (a wide variety of drugs ranging from non-peptide/non-protein drugs, including low-molecular-weight drugs, to peptide/protein drugs) as the preparations of the present invention is sprayed under the same conditions.

As described above, the present invention improves the productivity of preparations as well as the efficiency and uniformity of spraying preparations by nasal devices, and provides nasal preparations that achieve high drug absorption through nasal mucosa.

The invention claimed is:

1. A powdery nasal preparation comprising:
   a) a physiologically active substance; and
   b) a carrier, comprising a first crystalline cellulose, wherein the first crystalline cellulose has an average particle diameter of 30 μm or less and wherein the angle of repose of the powdery preparation is 53° or less.

2. The carrier formulation of claim 1, wherein the angle of repose of the carrier is 40° to 53°.

3. The nasal preparation of claim 1, wherein the carrier further comprises a second crystalline cellulose or a starch.

4. The nasal preparation of claim 3, wherein the second crystalline cellulose or starch has an average particle diameter of 30 to 100 μm.

5. The nasal preparation of claim 3, wherein the second crystalline cellulose or starch is present from 5.0 to 30 (W/W) % of the carrier composition.

6. The nasal preparation of claim 1, wherein the carrier further comprises tribasic calcium phosphate.

7. The nasal preparation of claim 6, wherein the tribasic calcium phosphate has an average particle diameter of 100 μm or less.

8. The nasal preparation of claim 6, wherein the tribasic calcium phosphate is present from 0.5 to 5 (W/W) % of the carrier composition.

9. The nasal preparation of claim 1, wherein the first crystalline cellulose is present from 60 to 94.9 (W/W) % of the carrier composition.

10. The nasal preparation of claim 1, wherein the physiologically active substance is present at a weight ratio of 0.0001 to 1.2 to the total weight of the carrier in its free form without being converted to the salt form, when the total weight of the carrier is taken as 1.

11. The nasal preparation of claim 1, wherein the physiologically active substance is a peptide/protein drug.

12. The nasal preparation of claim 11, wherein the peptide/protein drug is selected from the group consisting of insulin, growth hormone, growth hormone releasing peptide, ghrelin, glucagon, calcitonin, interferon, erythropoietin, interleukin, PTH(1-84), PTH(1-34), PTH-related peptide, GLP-1, vasopressin, leuprorelin, granulocyte-colony stimulating factor, prolactin, human menopausal gonadotropin, chorionic gonadotropin, follicle stimulating hormone, luteinizing hormone, leptin, nerve growth factor (NGF), stem cell growth factor (SCGF), keratinocyte growth factor (KGF), thioredoxin, cyclosporin, and influenza vaccine.

13. The nasal preparation of claim 11, wherein the peptide/protein drug is selected from growth hormone, glucagon, calcitonin, parathyroid hormone(1-84), parathyroid hormone (1-34) and PTH-related peptide.

14. The nasal preparation of claim 1, wherein the physiologically active substance is a non-peptide/non-protein drug.

15. The nasal preparation of claim 14, wherein the non-peptide/non-protein drug is selected from the group consisting of morphine, fentanyl, oxycodone, butorphanol, tramadol, granisetron, ondansetron, tropisetron, palonosetron, indisetron, sumatriptan, zolmitriptan, rizatriptan, naratriptan, ergotamine, triazolam, melatonin, carbamazepine, midazolam, donepezil, tiapride, cefaclor, enoxacin, aciclovir, zidvudine, didanosine, nevirapine, indinavir, dantrolene, digoxin, trihexyphenidyl, biperiden, dextromethorphan, naloxone, betahistine, naphazoline, diltiazem, tranilast, loperamide, diclofenac, beclomethasone, chlorpheniramine, sildenafil, vardenafil, cyanocobalamin, finasteride, epinephrine, 5-fluorouracil (5-FU), low-molecular-weight heparin, tacrolimus, RNA, RNAi, siRNA, antisense DNA, and allergen extract powder.

16. The nasal preparation of claim 14, wherein the non-peptide/non-protein drug is selected from fentanyl, oxycodone, granisetron, ondansetron, sumatriptan and zolmitriptan.

17. The nasal preparation of claim 1, further comprising a pH adjustor, preservative, stabilizer, flavor, absorbefacient, or substance that captures a divalent calcium ion.

18. A powdery carrier formulation for nasal administration wherein the angle of repose of the carrier formulation is 35° to 55°, wherein the carrier comprises a first crystalline cellulose having an average particle diameter of 30 µm or less.

19. The carrier formulation of claim 18, wherein the angle of repose of the carrier formulation is 40° to 53°.

20. The carrier formulation of claim 18, wherein the carrier further comprises a second crystalline cellulose or a starch.

21. The carrier formulation of claim 20, wherein the second crystalline cellulose or starch has an average particle diameter of 30 to 100 µm.

22. The carrier formulation of claim 20, wherein the second crystalline cellulose or starch is present from 5.0 to 30 (W/W) % of the total composition.

23. The carrier formulation of claim 18, wherein the carrier further comprises tribasic calcium phosphate.

24. The carrier formulation of claim 23, wherein the tribasic calcium phosphate has an average particle diameter of 100 µm or less.

25. The carrier formulation of claim 23, wherein the tribasic calcium phosphate is present from 0.1 to 10 (W/W) % of the total composition.

26. The carrier formulation of claim 18, wherein the first crystalline cellulose is present from 60 to 94.9 (W/W) % of the total composition.

27. A nasal preparation, which comprises at least a complex of a physiologically active substance and a powder flowability-improving component comprising:

(i) crystalline cellulose (A), which is a first crystalline cellulose with an untapped bulk density of 0.13 to 0.29 g/cm$^3$, a specific surface area of 1.3 m$^2$/g or more, an average particle diameter of 30 µm or less, and an angle of repose of 55° or more;
(ii) tribasic calcium phosphate (B); and
(iii) crystalline cellulose (C), which is a second crystalline cellulose with an untapped bulk density of 0.26 to 0.48 g/cm$^3$, a specific surface area of 1.3 m$^2$/g or less, an angle of repose of 50° or less, and an average particle diameter of 150 µm or less, or starch (D) with an untapped bulk density of 0.35 to 0.65 g/cm$^3$, a specific surface area of 1.3 m$^2$/g or less, an angle of repose of 55° or less, and an average particle diameter of 150 µm or less; wherein the flowability-improving component comprises 0.1 to 10 (W/W) % tribasic calcium phosphate (B), 5.0 to 30 (W/W) % second crystalline cellulose (C) and/or starch (D), and the remainder is the first crystalline cellulose (A); and the nasal preparation comprises the physiologically active substance at a weight ratio of 0.0001 to 1.2 to the total weight of the powder flowability-improving component in its free form without being converted to the salt form, when the total weight of the flowability-improving component is taken as 1.

28. The nasal preparation of claim 27, wherein the angle of repose of the nasal preparation is 53° or less.

29. The nasal preparation of claim 27, wherein the physiologically active substance is a peptide/protein drug.

30. The nasal preparation of claim 29, wherein the peptide/protein drug is selected from the group consisting of insulin, growth hormone, growth hormone releasing peptide, ghrelin, glucagon, calcitonin, interferon, erythropoietin, interleukin, PTH(1-84), PTH(1-34), PTH-related peptide, GLP-1, vasopressin, leuprorelin, granulocyte-colony stimulating factor, prolactin, human menopausal gonadotropin, chorionic gonadotropin, follicle stimulating hormone, luteinizing hormone, leptin, nerve growth factor (NGF), stem cell growth factor (SCGF), keratinocyte growth factor (KGF), thioredoxin, cyclosporin, and influenza vaccine.

31. The nasal preparation of claim 29, wherein the peptide/protein drug is selected from growth hormone, glucagon, calcitonin, parathyroid hormone(1-84), parathyroid hormone (1-34) and PTH-related peptides.

32. The nasal preparation of claim 27, wherein the physiologically active substance is a non-peptide/non-protein drug.

33. The nasal preparation of claim 32, wherein the non-peptide/non-protein drug is selected from the group consisting of morphine, fentanyl, oxycodone, butorphanol, tramadol, granisetron, ondansetron, tropisetron, palonosetron, indisetron, sumatriptan, zolmitriptan, rizatriptan, naratriptan, ergotamine, triazolam, melatonin, carbamazepine, etizolam, midazolam, donepezil, tiapride, cefaclor, enoxacin, aciclovir, zidvudine, didanosine, nevirapine, indinavir, dantrolene, digoxin, trihexyphenidyl, biperiden, dextromethorphan, naloxone, betahistine, naphazoline, diltiazem, tranilast, loperamide, diclofenac, beclomethasone, chlorpheniramine, sildenafil, vardenafil, cyanocobalamin, finasteride, epinephrine, 5-FU, low-molecular-weight heparin, tacrolimus, RNA, RNAi, siRNA, antisense DNA, allergen extract powder, therapeutic agents for Parkinson's disease, and non-steroidal anti-inflammatory drugs (NSAIDs).

34. The nasal preparation of claim 32, wherein the non-peptide/non-protein drug is selected from fentanyl, oxycodone, granisetron, ondansetron, sumatriptan and zolmitriptan.

* * * * *